(12) United States Patent
Stefan et al.

(10) Patent No.: US 7,587,075 B1
(45) Date of Patent: Sep. 8, 2009

(54) VIRTUAL COSMETIC AND RECONSTRUCTIVE SURGERY SYSTEMS, METHODS, AND APPARATUSES

(75) Inventors: David B. Stefan, Chesapeake, VA (US); David A. Gilbert, Virginia Beach, VA (US)

(73) Assignee: Novaptus Systems, Incorporated, Chespeake, VA (US)

(*) Notice: Subject to any disclaimer, the term of this patent is extended or adjusted under 35 U.S.C. 154(b) by 901 days.

(21) Appl. No.: 11/103,072

(22) Filed: Apr. 11, 2005

Related U.S. Application Data

(63) Continuation-in-part of application No. 10/979,630, filed on Nov. 1, 2004, now Pat. No. 7,424,139.

(51) Int. Cl.
G06K 9/00 (2006.01)

(52) U.S. Cl. .................. 382/128; 382/131; 382/100; 382/225; 600/407; 600/427; 600/439; 600/523; 345/619

(58) Field of Classification Search .................. 709/107, 709/204, 223, 219, 315; 382/128, 131, 225, 382/262; 345/735, 751, 756, 155; 128/898; 600/411, 427
See application file for complete search history.

(56) References Cited

U.S. PATENT DOCUMENTS

| | | | |
|---|---|---|---|
| 5,687,737 A * | 11/1997 | Branham et al. ............. 600/523 |
| 5,704,791 A * | 1/1998 | Gillio .......................... 434/262 |
| 5,882,206 A * | 3/1999 | Gillio .......................... 434/262 |
| 6,161,080 A | 12/2000 | Aouni-Ateshian et al. |
| 6,190,320 B1 | 2/2001 | Lelong |
| 6,556,236 B1 | 4/2003 | Swift et al. |
| 6,608,628 B1 * | 8/2003 | Ross et al. ................... 345/619 |
| 6,614,921 B1 * | 9/2003 | Chung et al. ................ 382/131 |
| 7,236,817 B2 * | 6/2007 | Papas et al. ................. 600/427 |
| 7,324,668 B2 * | 1/2008 | Rubinstenn et al. ......... 382/118 |
| 7,424,139 B1 * | 9/2008 | Stefan et al. ................ 382/128 |
| 2002/0009214 A1 * | 1/2002 | Arima et al. ................ 382/128 |
| 2002/0035458 A1 | 3/2002 | Kim et al. |
| 2002/0064302 A1 | 5/2002 | Massengill |
| 2002/0092534 A1 * | 7/2002 | Shamoun .................... 128/898 |
| 2003/0023156 A1 | 1/2003 | Pappas et al. |

OTHER PUBLICATIONS

Interactive 3-D presentation of medical images on network using VRML 2.0; Sato et al. 1998.*

Canfield Introduces Breast Sculptor™ Surgical Modeling SoftwaRE, 2008.*

(Continued)

*Primary Examiner*—Vikkram Bali
*Assistant Examiner*—Nancy Bitar
(74) *Attorney, Agent, or Firm*—Bowman Green Hampton & Kelly, PLLC

(57) ABSTRACT

A method for producing a virtual forecasted model of a breast augmentation subject, comprising, receiving a preoperative subject's scanned image, wherein the scanned image comprises a three dimensional image, converting the scanned image from a scanned image format to a VRML image format, importing the converted VRML image into a VRML image editor, receiving, from a breast implant database, at least one modeled virtual breast implant, wherein the received virtual breast implant is selected based on a desired actual breast implant that is to be implanted in the preoperative subject, and embedding the received virtual breast implant in the preoperative subject's converted VRML image.

14 Claims, 25 Drawing Sheets

OTHER PUBLICATIONS

Way back machine for "www.axisthree.com"; May 24, 2004.*
Business description Portrait 3D, Nov. 2, 2003.*
Axis three Secures 1 million funding round and alliance with Siemens; Mar. 2004.*

Novaptus Offers New Way of Measuring Body Contours; *Hampton Roads Edition M.D. News Special Feature*; Anne A. Abraham; May 2004.

* cited by examiner

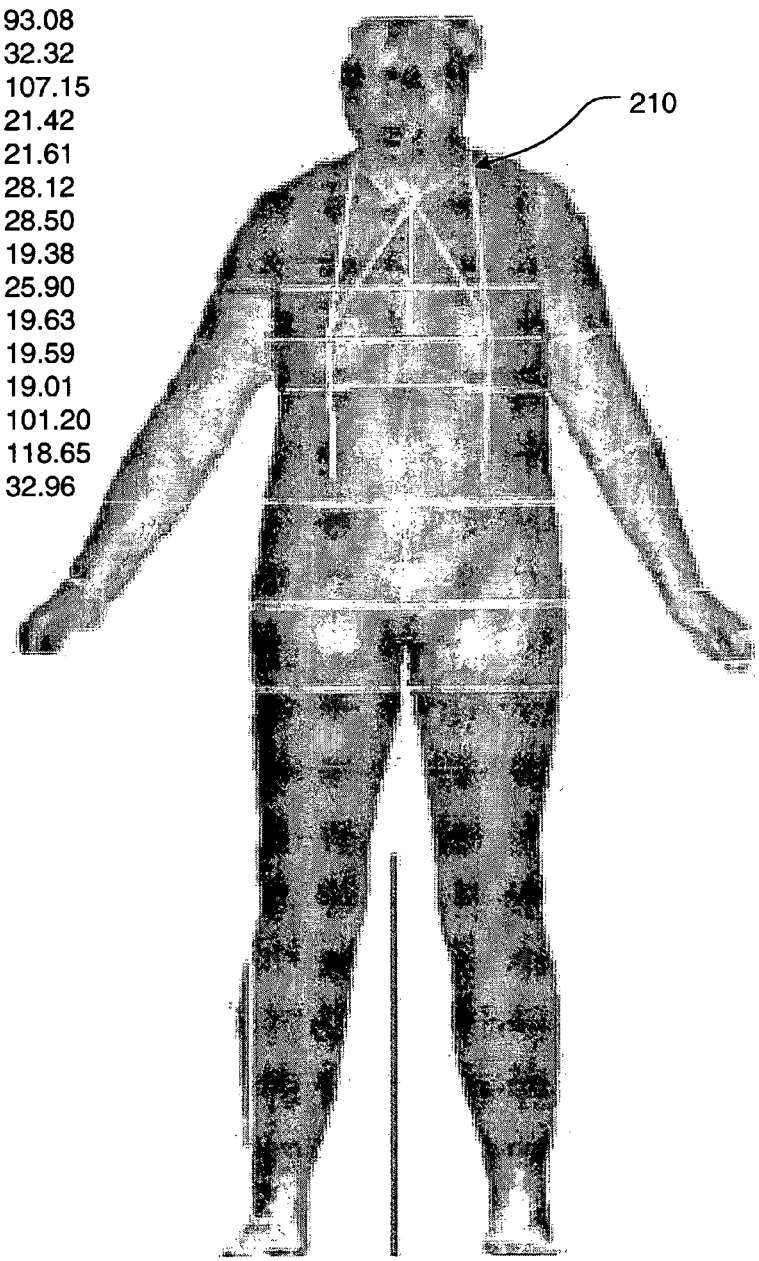

| Measurements | Units: cm |
|---|---|
| Top_Of_Head_Height | 153.11 |
| Bust_Full | 105.48 |
| Bust_Full(Contoured) | 107.98 |
| Bust_Height | 112.65 |
| Bust_Width | 32.61 |
| Bust_Prominance_Left | 28.87 |
| Bust_Prominance_Right | 28.84 |
| Underbust_Full | 93.08 |
| Underbust_Width | 32.32 |
| Underbust_Height | 107.15 |
| FrontNeck2Bust_Left | 21.42 |
| FrontNeck2Bust_Right | 21.61 |
| SideNeck2Bust_Left | 28.12 |
| SideNeck2Bust_Right | 28.50 |
| Neck2BustLine_Front | 19.38 |
| Neck2BustLine_Back | 25.90 |
| BustToWaist_Left | 19.63 |
| BustToWaist_Right | 19.59 |
| Bust2Bust_Horizontal | 19.01 |
| Chest_Full | 101.20 |
| Chest_Height | 118.65 |
| Chest_Width | 32.96 |

*FIG. 2*

Preoperative Image | Left Breast Reduced by 227 cc | Right Breast Reduced by 250 cc

| Size | |
|---|---|
| X | 45.8 |
| Y | 76.3 |
| Z | 31.5 |
| Proportional | ◉ |
| Percentage | 100.0 |
| Volume | 53967. |
| Surface | 7066.1 |

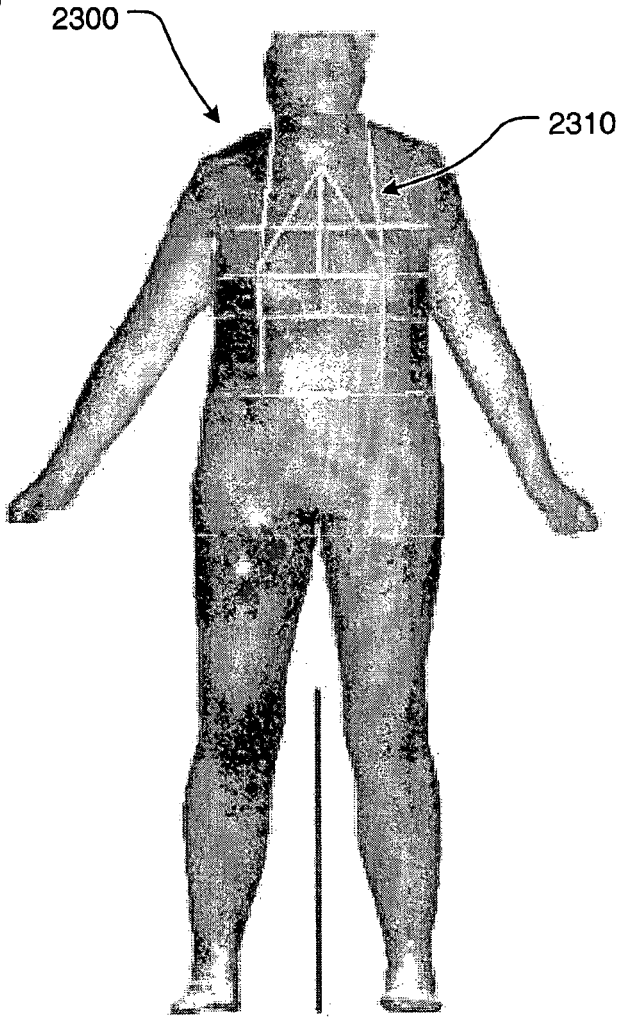

| Measurements | Units: cm |
|---|---|
| Top_Of_Head_Height | 151.49 |
| Bust_Full | 104.38 |
| Bust_Full(Contoured) | 106.62 |
| Bust_Height | 112.62 |
| Bust_Width | 32. |
| Bust_Prominance_Left | 29.19 |
| Bust_Prominance_Right | 28.18 |
| Underbust_Full | 92.32 |
| Underbust_Width | 31.93 |
| Underbust_Height | 106.62 |
| FrontNeck2Bust_Left | 21.86 |
| FrontNeck2Bust_Right | 21.8 |
| SideNeck2Bust_Left | 30.76 |
| SideNeck2Bust_Right | 32.73 |
| Neck2BustLine_Front | 19.91 |
| Neck2BustLine_Back | 26.27 |
| BustToWaist_Left | 18.06 |
| BustToWaist_Right | 18. |
| Bust2Bust_Horizontal | 18.51 |
| Chest_Full | 100.59 |
| Chest_Height | 118.37 |
| Chest_Width | 32.54 |

*FIG. 23*

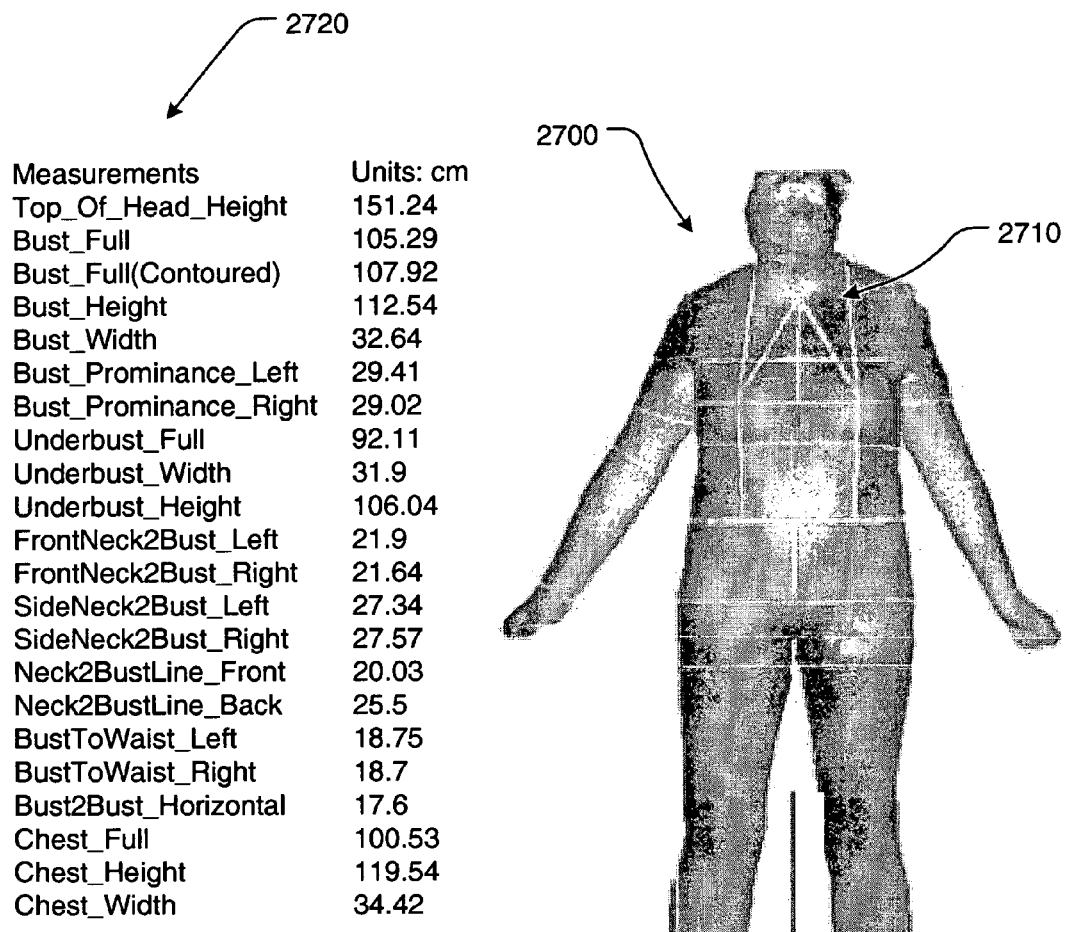

| Measurements | Units: cm |
|---|---|
| Top_Of_Head_Height | 151.24 |
| Bust_Full | 105.29 |
| Bust_Full(Contoured) | 107.92 |
| Bust_Height | 112.54 |
| Bust_Width | 32.64 |
| Bust_Prominance_Left | 29.41 |
| Bust_Prominance_Right | 29.02 |
| Underbust_Full | 92.11 |
| Underbust_Width | 31.9 |
| Underbust_Height | 106.04 |
| FrontNeck2Bust_Left | 21.9 |
| FrontNeck2Bust_Right | 21.64 |
| SideNeck2Bust_Left | 27.34 |
| SideNeck2Bust_Right | 27.57 |
| Neck2BustLine_Front | 20.03 |
| Neck2BustLine_Back | 25.5 |
| BustToWaist_Left | 18.75 |
| BustToWaist_Right | 18.7 |
| Bust2Bust_Horizontal | 17.6 |
| Chest_Full | 100.53 |
| Chest_Height | 119.54 |
| Chest_Width | 34.42 |

*FIG. 27*

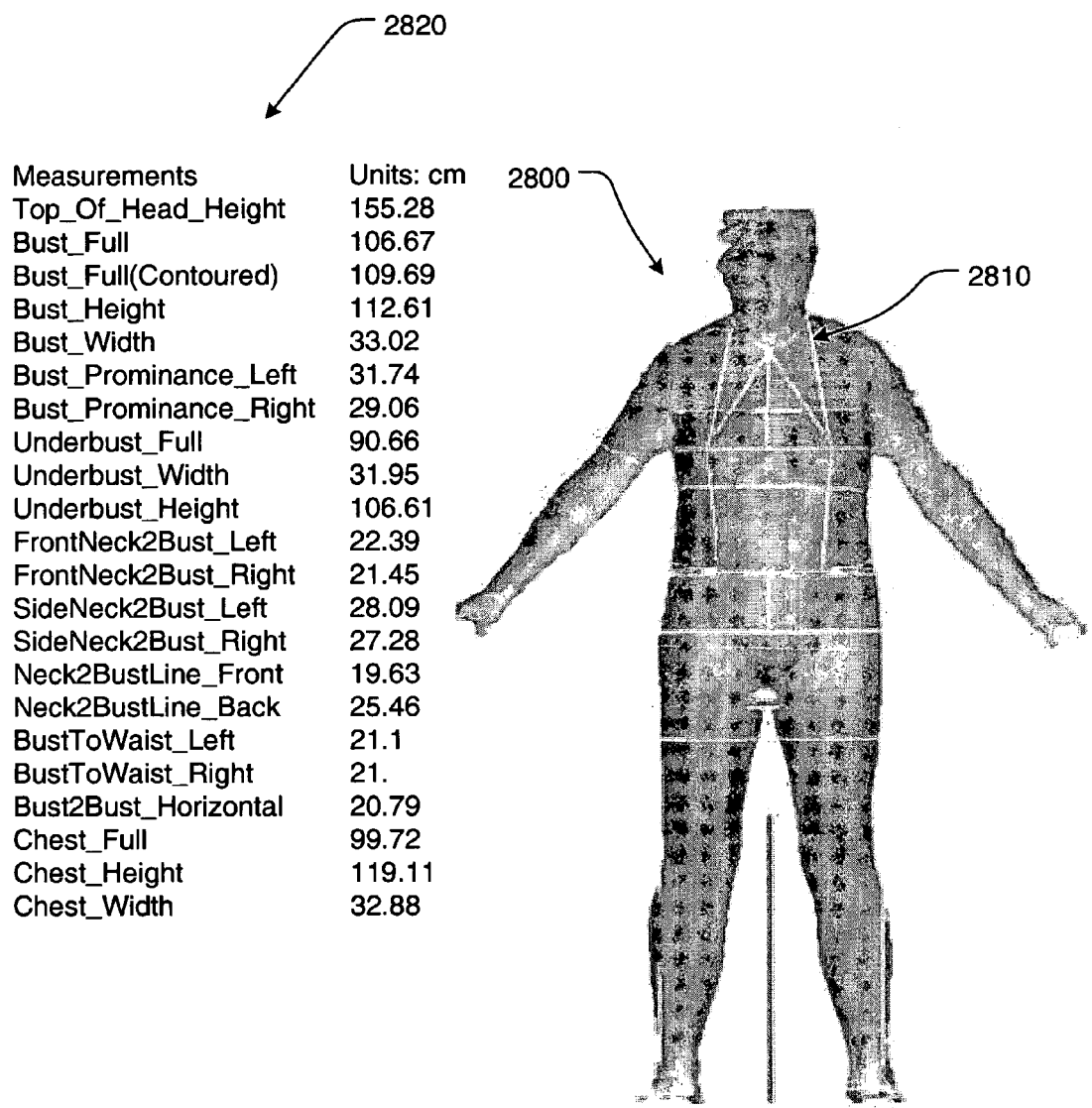

| Measurements | Units: cm |
|---|---|
| Top_Of_Head_Height | 155.28 |
| Bust_Full | 106.67 |
| Bust_Full(Contoured) | 109.69 |
| Bust_Height | 112.61 |
| Bust_Width | 33.02 |
| Bust_Prominance_Left | 31.74 |
| Bust_Prominance_Right | 29.06 |
| Underbust_Full | 90.66 |
| Underbust_Width | 31.95 |
| Underbust_Height | 106.61 |
| FrontNeck2Bust_Left | 22.39 |
| FrontNeck2Bust_Right | 21.45 |
| SideNeck2Bust_Left | 28.09 |
| SideNeck2Bust_Right | 27.28 |
| Neck2BustLine_Front | 19.63 |
| Neck2BustLine_Back | 25.46 |
| BustToWaist_Left | 21.1 |
| BustToWaist_Right | 21. |
| Bust2Bust_Horizontal | 20.79 |
| Chest_Full | 99.72 |
| Chest_Height | 119.11 |
| Chest_Width | 32.88 |

*FIG. 28*

VIRTUAL COSMETIC AND RECONSTRUCTIVE SURGERY SYSTEMS, METHODS, AND APPARATUSES

CROSS-REFERENCE TO RELATED APPLICATIONS

This is a Continuation-in-Part of U.S. patent application Ser. No. 10/979,630, filed Nov. 1, 2004 now U.S. Pat. No. 7,424,139, the entire disclosure of which is incorporated herein by reference.

BACKGROUND OF THE INVENTION

Field of the Invention

This invention relates generally to cosmetic and reconstructive surgery. In particular, the present invention relates to improved virtual cosmetic and reconstructive surgery systems, methods, and apparatuses.

SUMMARY OF THE INVENTION

The present invention relates generally to cosmetic and reconstructive surgery. In particular, the present invention relates to improved virtual cosmetic and reconstructive surgery systems, methods, and apparatuses.

Known methods for evaluating subjects and potential subjects for cosmetic and reconstructive surgery are not able to provide the subjects and potential subjects with accurate forecasting and modeling of expected results and outcomes.

The virtual surgery systems, methods, and apparatuses of this invention allow a user to predict, evaluate, and validate various cosmetic and reconstructive surgical procedures. In an illustrative, non-limiting embodiment of this invention, the virtual surgery systems, methods, and apparatuses allow a user to predict, evaluate, and validate various breast augmentation surgical procedures.

In an illustrative, non-limiting embodiment of this invention, the virtual surgery systems, methods, and apparatuses utilize a scanner, such as, for example, a white light scanner, measurement software, queries to a postoperative breast augmentation catalog, conversion of the preoperative image to an appropriate native three-dimensional (3D) data modeling language, such as, for example, Virtual Reality Modeling Language (VRML) image, grafting and scaling of chosen postoperative breast augmentation subjects to produce a forecasted VRML image, conversion of the forecasted VRML image to a format readable by the scanner, and finally, measuring the forecasted VRML image with certain scanner measurement software.

In various exemplary embodiments of this invention, if no suitable matches are returned when querying the postoperative breast augmentation catalog, or matches that have been returned are rejected by the surgeon and/or the preoperative subject, such that a desired postoperative breast augmentation subject is not chosen, a virtual surgeon can perform virtual breast augmentation on the preoperative subject's 3D scan image using the methods of this invention to produce one or more forecasted models or VRML images.

After a surgical procedure is performed, postoperative scans of the subject may be compared to the forecasted VRML images for validation purposes. The postoperative scan or scans may be added to the catalog of postoperative subjects.

Accordingly, this invention provides virtual surgery systems, methods, and apparatuses, which are capable of evaluating subjects and potential subjects for cosmetic and reconstructive surgery.

This invention separately provides virtual surgery systems, methods, and apparatuses, which provide subjects and potential subjects for cosmetic and reconstructive surgery with accurate forecasting and modeling of expected results and outcomes.

This invention separately provides virtual surgery systems, methods, and apparatuses, which allow a user to predict, evaluate, and validate various cosmetic and reconstructive surgical procedures.

These and other features and advantages of this invention are described in or are apparent from the following detailed description of the exemplary embodiments.

BRIEF DESCRIPTION OF THE DRAWINGS

The exemplary embodiments of this invention will be described in detail, with reference to the following figures, wherein like reference numerals refer to like parts throughout the several views, and wherein:

FIG. 2 shows the scanned image of the preoperative breast augmentation subject, and the associated measurements extracted by the procedure-specific measurement extraction profile;

FIG. 23 shows the forecasted model converted into scanner software format, measured with the same MEP used to measure the preoperative subject's scanned image;

FIG. 27 shows the modified forecasted model converted scan image, along with associated measurements;

FIG. 28 shows the subject's two-week postoperative scan and associated measurements;

DETAILED DESCRIPTION OF AN EXEMPLARY EMBODIMENT

For simplicity and clarification, the design factors and operating principles of the virtual surgery systems, methods, and apparatuses of this invention are explained with reference to various exemplary embodiments of virtual surgery systems, methods, and apparatuses of this invention. The basic explanation of the design factors and operating principles of the virtual surgery systems, methods, and apparatuses is applicable for the understanding, design, and operation of the virtual surgery systems, methods, and apparatuses of this invention.

Furthermore, it should be appreciated that, for simplicity and clarification, the embodiments of this invention will be described with reference to the prediction, evaluation, and validation of an exemplary breast augmentation surgical procedure. However, it should be appreciated that the virtual surgery systems, methods, and apparatuses of this invention may be utilized in various other cosmetic and reconstructive surgical procedures, wherein tissue or fluid is to be removed from or added to a subject, when the subject's body contours are altered or manipulated.

Thus, it should be appreciated that the systems and methods of this invention may be implemented to predict, evaluate, and validate any type of body contouring, cosmetic, or reconstructive surgical procedures.

It should also be appreciated that, for simplicity and clarification, the embodiments of this invention will be described with reference to the use of VRML image editing tools to manipulate various scan images and/or models. However, it should be appreciated that the virtual surgery systems and methods of this invention may utilize any appropriate native 3D data modeling language, such as, for example VRML, Amapi, 3D Studio, Wavefront, STL, IGES, AutoCAD, Open Inventor, Illustrator, or any known or later developed 3D data modeling language capable of being used to manipulate the various scan images and/or models.

Furthermore, the embodiments of this invention will be described with reference to a "virtual surgeon" manipulating certain images and acting to effect the virtual surgery systems and methods of this invention. It should be understood that the "virtual surgeon" may be a human actor, a computer or computer program, or a combination of human and computer interactions. Therefore, the term "virtual surgeon" is not to be construed as limiting the virtual surgery systems and methods of this invention.

It should also be appreciated that the term "virtual surgery" is for a basic explanation and understanding of the operation of the virtual surgery systems and methods of this invention. Therefore, the term "virtual surgery" is not to be construed as limiting the virtual surgery systems and methods of this invention.

Figure 1A:
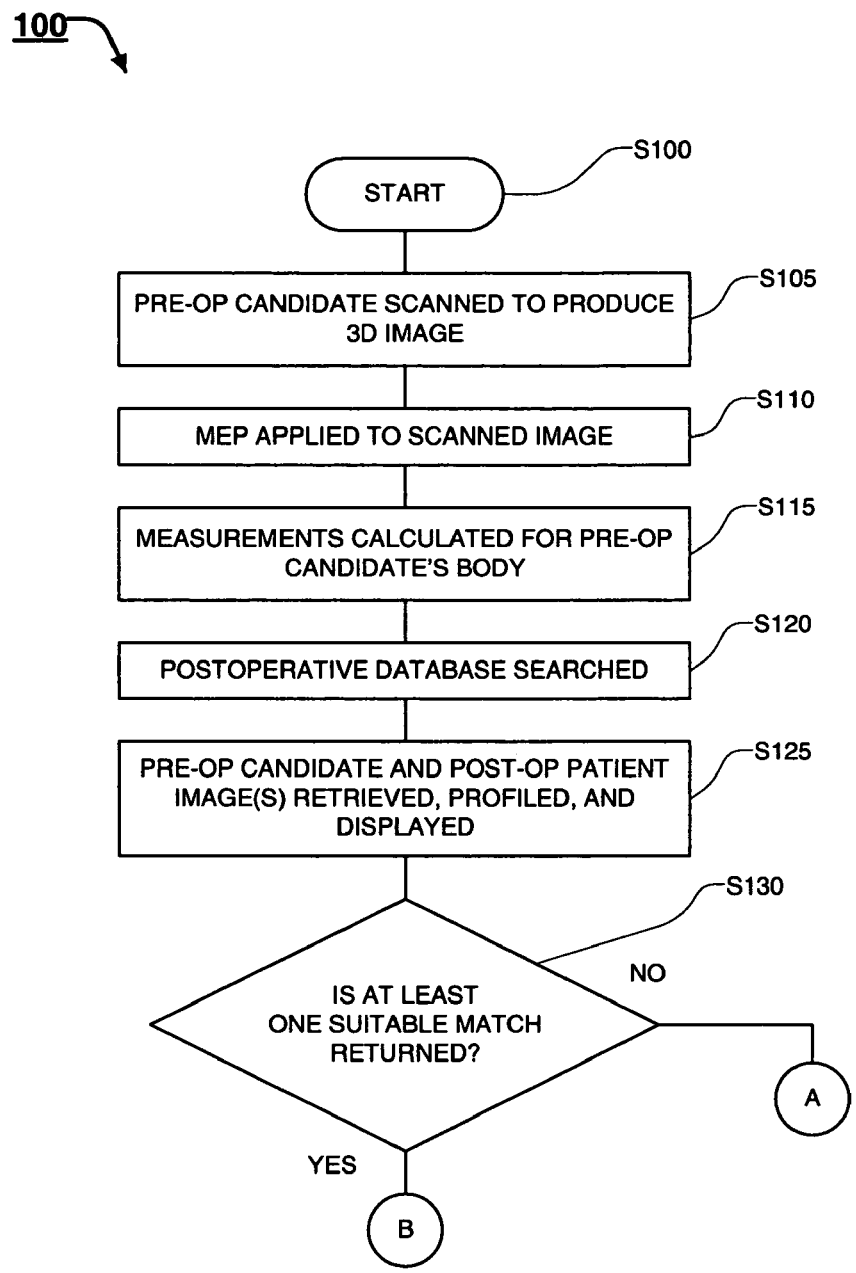
FIGS. 1A, 1B, and 1C show a flowchart outlining one illustrative, non-limiting embodiment of a method for performing virtual surgery according to this invention.
Figure 1B:
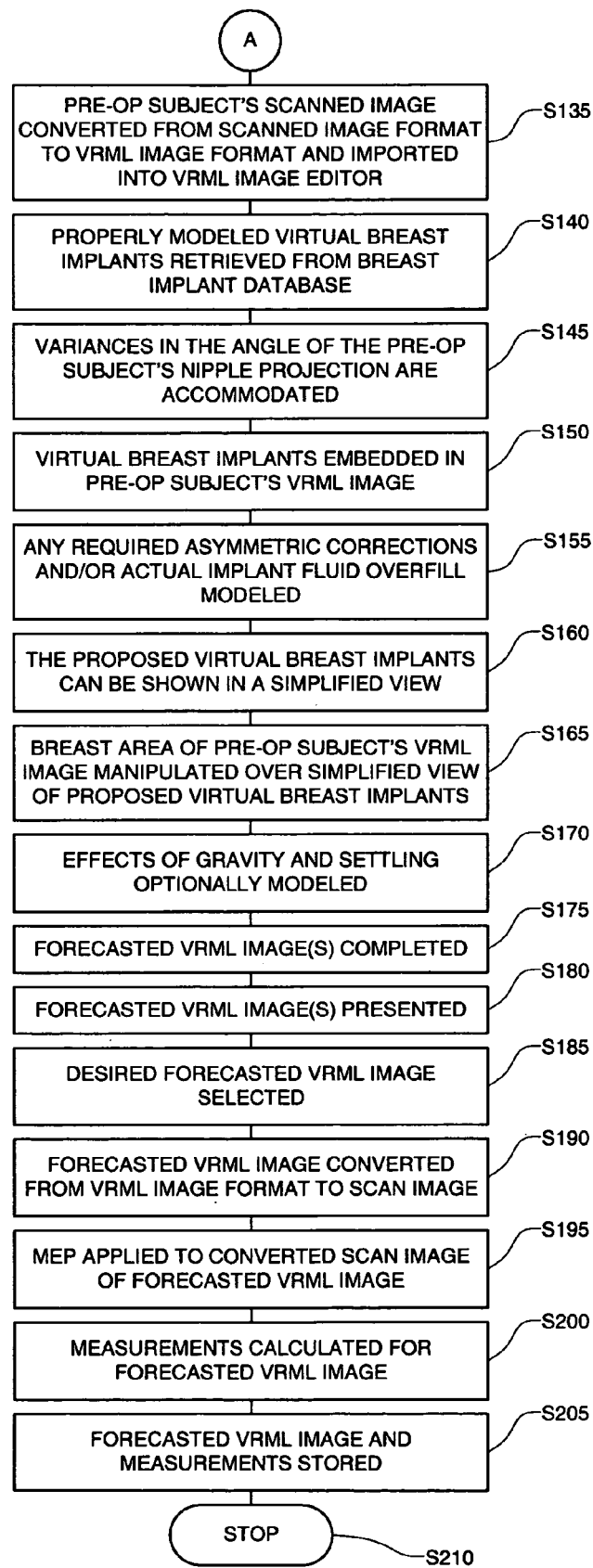
Figure 1C:
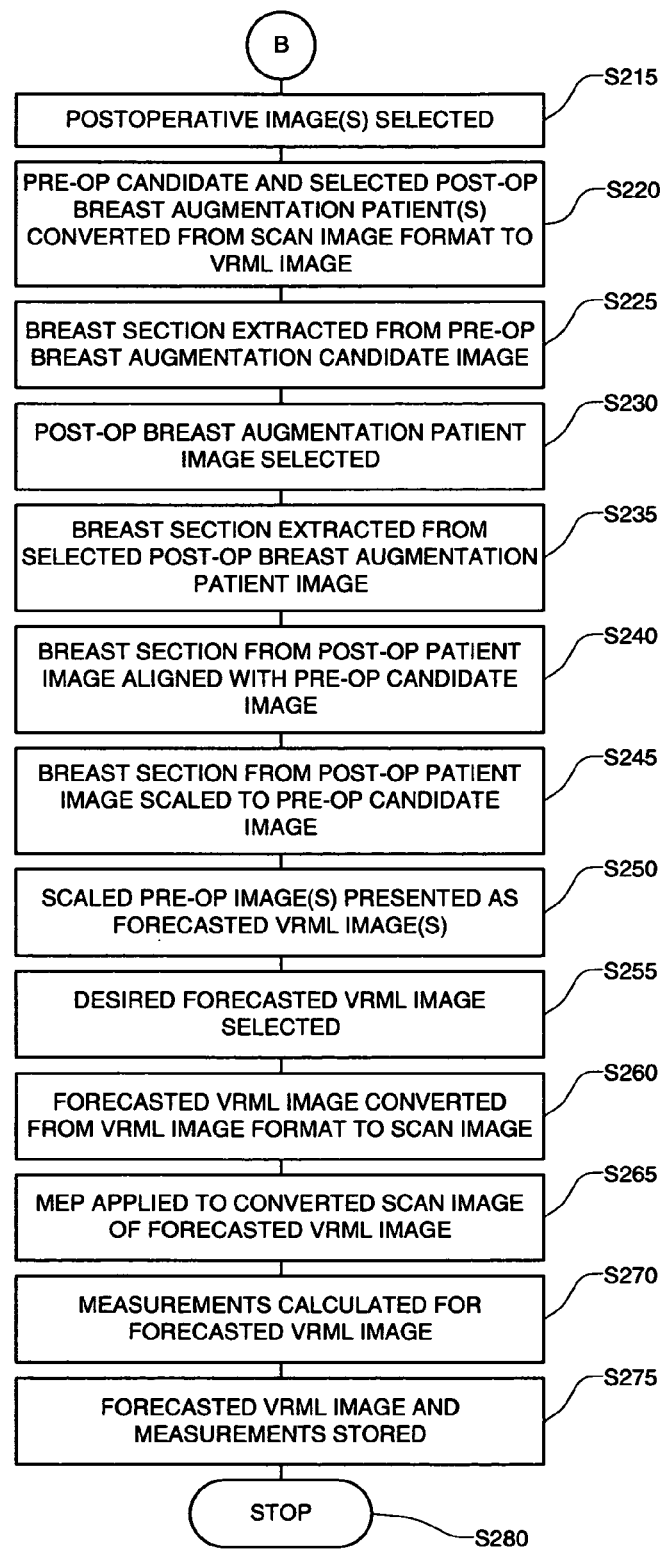

FIGS. 1A, 1B, and 1C show a flowchart 100 outlining one illustrative, non-limiting embodiment of a method for performing virtual surgery according to this invention.

As shown in FIGS. 1A, 1B, and 1C, the exemplary method begins in step S100 and continues to Step S105 wherein a preoperative subject's body is scanned to produce a highly accurate, dimensionally correct, 3D image of the preoperative subject's body. In various exemplary embodiments, a white light scanner is used to produce the scanned image. However, it should be appreciated that in various exemplary embodiments, and laser, ultrasonic, or other appropriate scanner, capable of providing a highly accurate, dimensionally correct, 3D image of the preoperative subject's body may be used.

Then, in Step S110, a specialized measurement template, or Measurement Extraction Profile (MEP), is applied to the preoperative subject's scanned image. This MEP file contains instructions for determining specific measurements of the preoperative subject's scanned image.

Next, in Step S115, the MEP file is used to calculate key measurements of the preoperative subject's scanned image, such as, for example, of the subject's breasts, waist, hips, abdomen, and stomach. Additionally, certain straight line measurements are calculated for the chest, bust, underbust, waist, hips, abdomen, and stomach. These straight line measurements form the guidelines for selecting appropriate postoperative breast augmentation subjects.

In Step S120, a postoperative catalog database is searched for previously scanned and measured postoperative breast augmentation subjects whose key measurements, as determined by the MEP file, are similar to the key measurements of the preoperative subject. In various exemplary embodiments, certain chest, bust, underbust, abdominal, and other straight line and/or width measurements are compared between the preoperative subject and the cataloged postoperative breast augmentation subjects to determine similar key measurements.

In various exemplary embodiments, the database is not searched for exact measurement matches. Rather, the search and comparison parameters are such that postoperative catalog database subjects having selected measurements within a specified range are identified.

In various exemplary embodiments, additional information may be associated with the postoperative subject's scan image. For example, information regarding the implant sizes that the postoperative subject received, the postoperative subject's age at the time of the procedure, any relevant medical data that indicates special conditions that the postoperative subject may have that could eliminate the subject for consideration, and the like.

In Step S125, the preoperative subject's scanned image and the appropriate postoperative subjects' scanned images are retrieved, profiled, and displayed.

In Step S130, a determination is made as to whether at least one acceptable postoperative subject's scanned image has been retrieved, profiled, and displayed. If, in Step S130, it is determined that no acceptable postoperative subject's scanned image has been retrieved, profiled, and displayed, the method advances to Step S135. Otherwise, if at least one acceptable postoperative subject's scanned image has been retrieved, profiled, and displayed, the method jumps to Step S215.

In Step S130, a determination that no acceptable postoperative subject's scanned image has been retrieved, profiled, and displayed may be made because no suitable matches are returned when querying the postoperative breast augmentation catalog. Alternatively, the surgeon and/or the preoperative subject may not be pleased with the matches that have been returned and may reject the returned matches.

In these instances, a virtual surgeon can perform virtual breast augmentation on the preoperative subject's 3D image by embedding properly modeled virtual breast implants in the preoperative subject's 3D image using the following method steps. The virtual embedding process produces one or more forecasted models.

In Step S135, the preoperative subject's scanned image is converted from the scanned image format to a VRML image format and imported into a VRML image editor.

In Step S140, a breast implant database is searched for properly modeled virtual breast implants. Because breast implants have known dimensions, virtual breast implants can be accurately modeled by, for example, a native 3D data editor. The breast implant database comprises a library of modeled virtual breast implants, which include the surface area and volume measurements for each of the virtual breast implants, such that the virtual breast implants can be used and manipulated by a VRML editor. In various exemplary embodiments, appropriate virtual breast implants are selected based on the desired actual breast implants that are to be implanted in the preoperative subject.

Once appropriate, proposed virtual breast implants are selected, the method advances to Step S140, and the virtual surgeon positions the proposed virtual breast implants on the preoperative subject's VRML image chest wall, using the VRML image editor. In various exemplary embodiments, this is accomplished by applying certain surface area, volume, and linear measurements to the preoperative subject's VRML image for each of the virtual breast implants.

Then, in Step S145, the virtual surgeon accommodates variances in the angle of the preoperative subject's nipple projection by rotating the proposed virtual breast implants on the preoperative subject's VRML image chest wall.

Next, in Step S150, the virtual surgeon uses stretching and shaping functions to manipulate the splines of the subject's VRML image to embed the virtual breast implants in the preoperative subject's VRML image.

It should be appreciated that, in various exemplary embodiments, the embedding process may be performed multiple times on multiple VRML images of the preoperative subject, prior to the actual surgery, to develop multiple forecasted models.

In Step S155, any required asymmetric corrections and/or actual implant fluid overfill can be modeled. Any required asymmetric corrections can be modeled using mathematical calculations that vary the size and volume of each virtual breast implant prior to and during the embedding process.

Modeling actual implant fluid overfill can be accomplished by manipulating the appropriate splines around the area of each virtual breast implant, after the virtual breast implant in embedded.

Once the proposed virtual breast implants are positioned on the chest wall of the preoperative subject's VRML image, the method advances to Step S160 and the proposed virtual breast implants can be shown in a simplified view. The simplified view transparently displays the outlines of the profile of the proposed virtual breast implants.

Then, in Step S165, the virtual surgeon uses stretching and shaping functions, either manually or automatically, via a software program, to manipulate the breast area points, edges, and facets of the preoperative subject's VRML image over the simplified view of the proposed virtual breast implants, one virtual breast implant at a time.

In Step S170, the effects of gravity and settling can optionally be modeled by relocating the coordinates of the nipple complex of the preoperative subject's VRML image and shaping certain splines around the image's torso implanted breast area.

It should be appreciated that, in various exemplary embodiments, the first virtual breast implant is virtually embedded in the preoperative subject's VRML image before the second virtual breast implant is virtually embedded in the preoperative subject's VRML image. Alternatively, both of the virtual breast implants can be virtually embedded in the preoperative subject's VRML image simultaneously.

The consequent changes in the torso volume and surface area of the preoperative subject's VRML image, once a virtual breast implants are embedded, closely predicts the volume and surface area of the actual implants within the shape of the preoperative subject's actual torso. The changes to the breast area of the preoperative subject's VRML image, as evidenced by the forecasted model(s), closely predicts the actual volume, surface area, and the new breast contours the preoperative subject would actually have, forecasting the aesthetic outcome of the actual surgical procedure.

Once the virtual embedding process is complete, the method advances to Step S175 and a completed forecasted VRML model is produced. It should be appreciated that the virtual embedding process may be repeated, as desired, to produce multiple completed forecasted VRML models, each of which reflects a different virtual breast augmentation size, predicted or forecasted breast contour shape, and/or procedure.

If, in Step S175, multiple completed forecasted VRML models are produced, the method advances to Step S180 and the completed forecasted VRML models are presented to the preoperative subject as a forecasted VRML image of the preoperative subject after the actual breast augmentation procedure is complete. Thus, in Step S180, the preoperative subject may be presented with a number of forecasted VRML images to review.

Then, in Step S185, the preoperative subject may review the forecasted VRML images, either alone or together with a surgeon, and select the best overall aesthetic forecasted VRML image that meets the desires of the subject, and the surgical guidelines, given the preoperative subject's overall body condition.

Once a forecasted VRML image is selected, the method jumps to Step S190 and the selected forecasted VRML image is converted from a VRML image to a format that a scanner can read and measure. In various exemplary embodiments, this is accomplished via a data converter. The data converter takes the forecasted VRML image, which is in VRML format, and converts the forecasted VRML image into a format that the scanner can interpret.

In Step S195, once a forecasted VRML image has been converted into a scanner readable format, the specialized MEP file, as applied in Step S110, is applied to the converted forecasted VRML image.

In Step S200, the specialized MEP file is used to measure the converted forecasted VRML image and calculate specific measurements of the preoperative subject's converted forecasted VRML image.

Then, in Step S205, once the specific measurements of the preoperative subject's converted forecasted VRML image have been calculated, the converted forecasted VRML image and the measurements become part of the preoperative subject's digital archive.

The method then advances to Step S210 and the method ends.

If, in Step S130, it was determined that at least one acceptable postoperative subjects' scanned image was retrieved, profiled, and displayed, the method jumps to Step S215

In Step S215, one or more appropriate postoperative breast augmentation subjects are selected from the retrieved possible postoperative subjects from the postoperative catalog database. The appropriate postoperative breast augmentation subjects may be selected based on, for example, prospective subjects whose breast shape and size appeals to the preoperative subject, makes aesthetic sense, and have similar dimensional widths as the preoperative subject. Additional information associated with the postoperative subject's scan image may also be used to determine the appropriate postoperative breast augmentation subjects.

It should be appreciated that in certain exemplary embodiments, a surgeon or other user may search the postoperative catalog database and select appropriate postoperative subjects. In other exemplary embodiments, the preoperative subject, with or without the assistance of the surgeon, may search the postoperative catalog database and select appropriate postoperative subjects. In still other exemplary embodiments, the search and selection may be performed either partially or entirely by an appropriate software program.

In Step S220, the preoperative subject's scanned image and the one or more selected postoperative breast augmentation subjects' scanned images are converted from the scanned image format to a VRML image format and imported into a VRML image editor.

Then, in Step S225, using the VRML image editor, an appropriate breast section is extracted from the torso of the preoperative subject's VRML image. It should be appreciated that in certain exemplary embodiments, a surgeon or other user may extract the appropriate breast section from the torso of the preoperative subject's VRML image. In other exemplary embodiments, the appropriate breast section may be extracted from the torso of the preoperative subject's VRML image either partially or entirely by an appropriate software program.

In various exemplary embodiments, selection of the appropriate breast section to be extracted is based on measurements that define the chest area and the abdominal/waist area of the preoperative subject's VRML image.

In Step S230, one of the one or more selected postoperative breast augmentation subjects is selected and, in Step S235, an appropriate breast section is extracted from the torso of the selected postoperative breast augmentation subject's VRML image using the VRML image editor. It should be appreciated that in certain exemplary embodiments, a surgeon or other user may extract an appropriate breast section from the torso of the selected postoperative subject's VRML image. In other exemplary embodiments, the appropriate breast section may be extracted from the torso of the selected postoperative breast augmentation subject's VRML image either partially or entirely by an appropriate software program.

In various exemplary embodiments, selection of the appropriate breast section to be extracted is based on measurements that define the chest area and the abdominal/waist area of each postoperative breast augmentation subject's VRML image.

Next, in Step S240, the postoperative breast augmentation subject's breast section is aligned within the preoperative subject's VRML image. In various exemplary embodiments, a surgeon or other user may align the breast section within the preoperative subject's VRML image. In other exemplary embodiments, the appropriate breast section may be aligned within the preoperative subject's VRML image either partially or entirely by an appropriate software program.

In Step S245, the postoperative breast augmentation subject's breast section is scaled, if necessary, to match the preoperative subject's torso. Scaling is typically necessary if the extracted breast section of the postoperative breast augmentation subject is dimensionally different from that of the preoperative subject's image. In various exemplary embodiments, the postoperative breast augmentation subject's breast section is scaled using a proportional scaling tool to enlarge the breast section in the X, Y, and Z axis to match the dimensions of the torso of the preoperative subject's VRML image. When proportional scaling is used, the implant sizes of the postoperative breast augmentation subject's implants are also proportionally scaled.

In various exemplary embodiments, a surgeon or other user may scale the breast section within the preoperative subject's VRML image. In other exemplary embodiments, the appropriate breast section may be scaled within the preoperative subject's VRML image either partially or entirely by an appropriate software program.

Then, in Step S250, the preoperative subject's image, with the postoperative breast augmentation subject's breast section having been aligned and scaled within the preoperative subject's VRML image, is presented to the preoperative subject as a forecasted VRML image of the preoperative subject after the breast augmentation procedure is complete.

It should be appreciated that the steps of selecting one of the one or more selected postoperative breast augmentation subjects; extracting an appropriate breast section from the selected postoperative breast augmentation subject's VRML image; aligning the postoperative breast augmentation subject's breast section within the preoperative subject's VRML image; scaling the postoperative breast augmentation subject's breast section, if necessary, to match the preoperative subject's torso; and presenting the preoperative subject's image, with the postoperative breast augmentation subject's breast section having been aligned and scaled within the preoperative subject's VRML image, to the preoperative subject as a forecasted VRML image (Step S230 through Step S250) may be repeated, as necessary, for any of the remaining one or more selected postoperative breast augmentation subjects' VRML images. In this manner a number of forecasted VRML images may be developed, which reflect different breast augmentation sizes and/or procedures based on selections from the postoperative breast augmentation catalog.

Thus, in Step S250, the preoperative subject may be presented with a number of forecasted VRML images to review.

In Step S255, the preoperative subject may review the forecasted VRML images, either alone or together with a surgeon, and select the best overall aesthetic forecasted VRML image that meets the desires of the subject, and the surgical guidelines, given the preoperative subject's overall body condition.

In Step S260, once a forecasted VRML image is selected, the selected forecasted VRML image is converted from a VRML image to a format that a scanner can read and measure. In various exemplary embodiments, this is accomplished via a data converter. The data converter takes the forecasted VRML image, which is in VRML format, and converts the forecasted VRML image into a format that the scanner can interpret.

In Step S265, once a forecasted VRML image has been converted into a scanner readable format, the specialized MEP file, as applied in Step S110, is applied to the converted forecasted VRML image.

In Step S270, the specialized MEP file is used to measure the converted forecasted VRML image and calculate specific measurements of the preoperative subject's converted forecasted VRML image.

Then, in Step S275, once the specific measurements of the preoperative subject's converted forecasted VRML image have been calculated, the converted forecasted VRML image and the measurements become part of the preoperative subject's digital archive.

The method then advances to Step S280 and the method ends.

It should be appreciated that each preoperative subject may have a digital archive established to allow information regarding the preoperative subject or subject, such as, for example, the preoperative subject/subject's various scans, images, and models, to be archived. Each digital archive may allow the preoperative subject/subject and/or doctors, surgeons, or other health-care providers easy reference to the preoperative subject/subject's various scans, images, and models.

In various exemplary embodiments, the entire virtual surgery process, as outlined herein, may be maintained in a digital archive and used as part of a subject maintenance program. As additional scans, images, and/or models of the preoperative subject/subject created, the digital archive and the subject maintenance program may be utilized, even apart from any surgical aspect, to provide an initial baseline and then allow for monitoring of the preoperative subject/subject's recovery, growth, and development over time.

It should be appreciated that although the method described above includes archiving, in Steps S205 and S275 the converted forecasted VRML image and the measurements as part of the preoperative subject's digital archive, each scan, image, and/or model created of or for the preoperative subject/subject may be included as part of the preoperative subject/subject's digital archive.

Furthermore, if the preoperative subject does have the surgical procedure, postoperative scans of the preoperative subject may be compared to the converted forecasted VRML image and the measurements for validation and so that any discrepancies may be identified and noted in appropriate digital archive data fields.

In various exemplary embodiments, the preoperative subject's postoperative scan may also be added to the breast augmentation catalog to be used to build future forecasted VRML images for other preoperative subjects.

FIG. 2 shows a first exemplary embodiment of a scanned preoperative image 200 of a preoperative subject with measurement lines 210 according to this invention.

As shown in FIG. 2, a preoperative subject's body has been scanned to produce a highly accurate, dimensionally correct, 3D image 200 of the preoperative subject's body. In various exemplary embodiments, a white light scanner is used to produce the scanned image 200. However, it should be appreciated that in various exemplary embodiments, a laser scanner, an ultrasonic imager, or any other known or later developed device useable for producing a highly accurate, dimensionally correct, 3D image of the preoperative subject's body may be used.

As further shown in FIG. 2, a specialized MEP has been applied to the scanned image 200 and certain measurement lines 210 have been applied to the preoperative scanned image 200 at, for example, the patient's chest, bust, underbust, waist, hips, abdomen, and stomach.

The chart 220, as also shown in FIG. 2, shows an exemplary summary of certain of the measurements extracted by the procedure-specific MEP file. The measurements outlined in the chart 220 include certain preoperative extracted measurements extrapolated from the scanned preoperative image 200.

Figure 3:
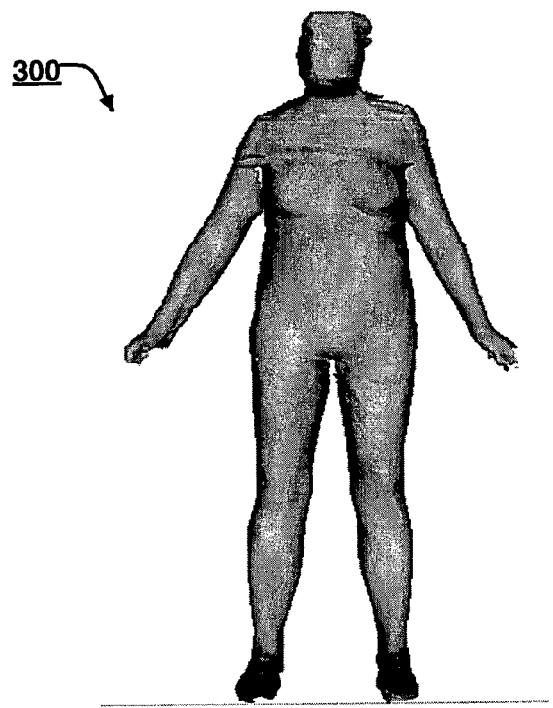
FIG. 3 shows the preoperative subject's scan image converted to VRML format, shown in smoothed view.

FIG. 3 shows the preoperative subject's scanned preoperative image 200 converted to VRML format to produce a preoperative VRML image 300. As shown in FIG. 3, the preoperative VRML image 300 is shown in a smoothed view. Once the preoperative subject's scanned preoperative image is converted to a preoperative VRML image, the preoperative VRML image is in a format for manipulation.

In this exemplary embodiment, the preoperative subject has old style gel implants that must be virtually extracted before new virtual breast implants can be embedded. By manipulating the points, edges, and facets of the preoperative subject's VRML image, a dimensionally and volumetrically accurate model can be produced that reflects the removal of the subject's existing implants.

Figure 4:
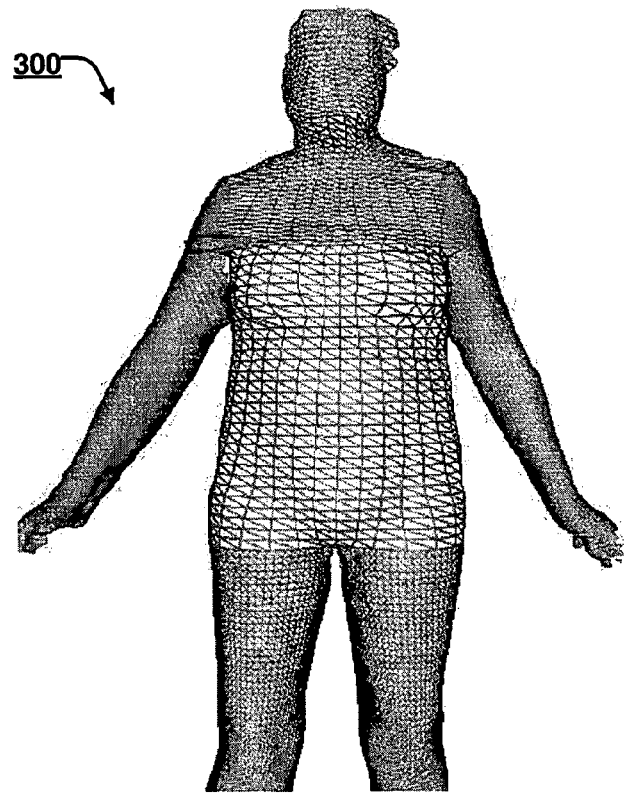
FIG. 4 shows the preoperative subject's VRML image as a collection of points, edges, and facets in 3D space.

FIG. 4 shows the subject's preoperative VRML image 300 as a collection of points, edges, and facets in 3D space.

Contiguous edges and facets are collectively known as splines. The act of manipulating the image's splines produce changes in the volume and surface area of the VRML image.

Figure 5:
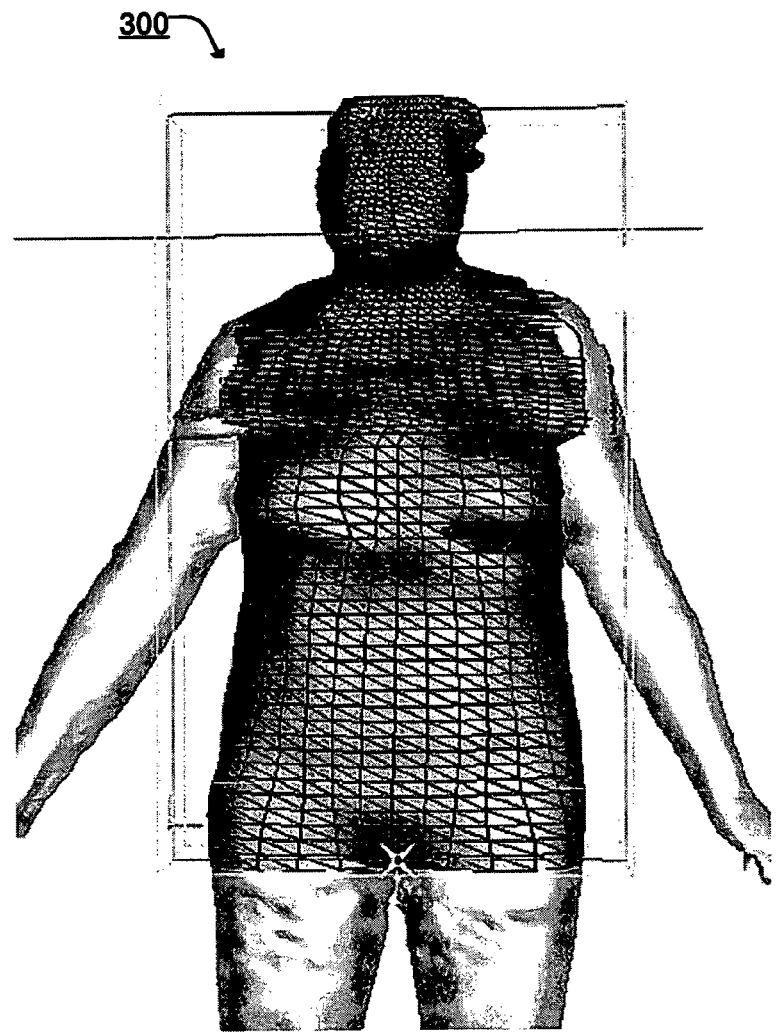
FIG. 5 shows the initial volume and surface area of the subject's preoperative VRML image.

FIG. 5 shows the subject's preoperative VRML image 300, wherein the initial volume and surface area of the preoperative subject's torso has been calculated. In this example, the preoperative subject's torso volume is approximately 54,444 cubic centimeters, and the surface area is approximately 7,168 centimeters, squared.

Once the initial volume and surface area of the preoperative subject's torso is calculated, the calculations can be recorded, for example, in the preoperative subject's digital archive.

Figure 6:
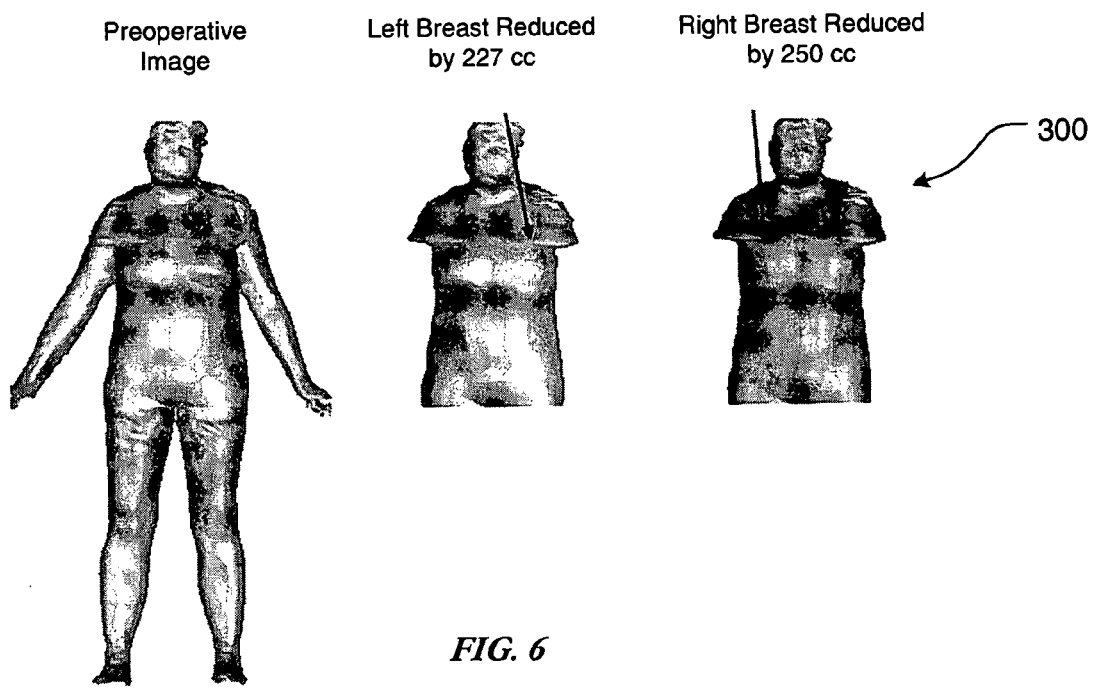
FIG. 6 shows the result of reducing the left breast, shown at the far left, by 227 cubic centimeters, and the right breast, shown as the middle figure, by 250 cubic centimeters, as compared to the subject's preoperative image.

The preoperative subject was known to have existing gel implants of 227 cubic centimeters in the left breast and 250 cubic centimeters in the right breast. Therefore, as shown in FIG. 6, the preoperative subject's torso is replicated the virtual explant process begins. This is done by manipulating the splines along each breast area, one breast at a time. In various exemplary embodiments, the image is placed in a supine position for the process.

To virtually explant the exiting breast implants, points on and around the breast are stretched along the z-axis (negative), resulting in a reduction of volume and surface area. Points along the x and y axis are manipulated to modify and form the contours of explanted breast shape.

FIG. 6 shows the results of reducing the left breast, shown at the far left, by 227 cubic centimeters, and the right breast, shown as the middle figure, by 250 cubic centimeters, as compared to the subject's preoperative VRML image 300.

Figure 7:
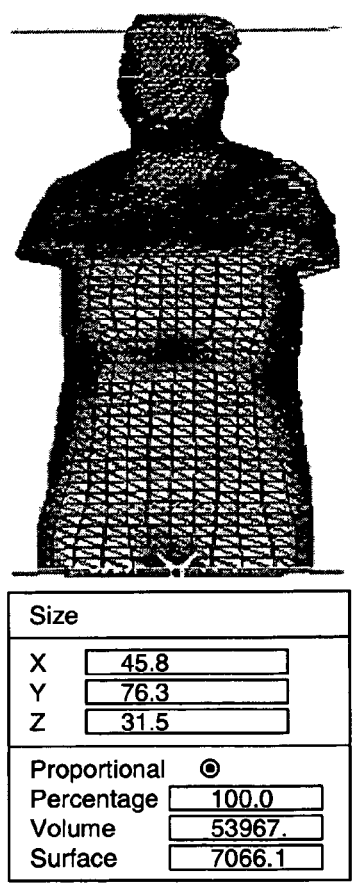
FIG. 7 shows the volume and surface area calculations of the torso that underwent the explant procedure.

FIG. 7 shows the volume and surface area calculations of the torso of the subject's preoperative VRML image 300, after having undergone the virtual explant procedure. In this example, the preoperative subject's torso volume, after the virtual explant procedure, is approximately 53,967 cubic centimeters, and the surface area is approximately 7,066 centimeters, squared. The torso volume and surface area calculations are recorded prior to placement of the proposed breast implants.

A comparison of the preoperative subject's torso and the breast implant extracted torso shows a volume reduction of approximately 477 cubic centimeters (227 cubic centimeters left, 250 cubic centimeters right) and a surface area reduction of approximately 102.6 centimeters, squared.

Figure 8:
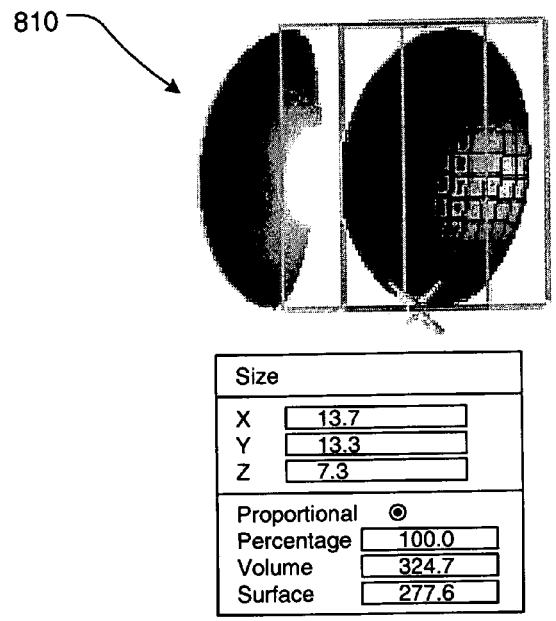
FIG. 8 shows the virtual breast implants created by the VRML editor, along with the dimensions and volume and surface area calculations.

FIG. 8 shows a virtual breast implant 810 created in the native 3D data modeler, such as, for example, a VRML editor, along with the dimensions and volume and surface area calculations for the virtual breast implant 810. The virtual breast implant 810 volumetrically and dimensionally approximates the actual implants.

It should be appreciated that a variety of virtual breast implants, along with the dimensions and volume and surface area calculations for the virtual breast implants, may be stored in a breast implant database.

As illustrated in FIG. 8, the exemplary virtual breast implant 810 has dimensions of approximately 13.5 cm, 13.5 cm, and 7.3 cm, and a volume of approximately 325 cubic centimeters.

There are instances when an actual surgeon deliberately overfills one or both breast implants either to accentuate the breast profile or to compensate for the subject's naturally asymmetric chest wall contours. In general, the amount of the overfill for each breast implant is normally not precisely known in advance of the surgery, rather, the actual surgeon has only a vague idea that the subject may require implant asymmetries to compensate variances within the subject's chest wall, or overcome a subject's ptotic breast condition.

However, using the systems and methods of this invention, a virtual surgeon can scale the virtual breast implants to model the predicted amount of overfill, if any, for each implant, prior to placement of the virtual breast implants on the chest wall of the subject's preoperative VRML image.

The virtual surgeon then produces one or more forecasted models, using symmetric and/or asymmetric virtual breast implant sizes, locating and embedding the implants using the procedure described herein. These forecasted models can be measured and presented to the actual surgeon for evaluation and guidance prior to the actual surgery and/or they may be shared with the subject to show overall aesthetic appeal of possible surgical outcomes.

It is not uncommon for the actual surgeon to make a decision regarding the amount of overfill for each implant during the actual operation. In the event that the virtual surgeon collaborates with the actual surgeon, either locally or via a remote link, and the actual surgeon chooses to deviate from the forecasted model, the virtual surgeon can scale each embedded virtual breast implant volume to match the amount of fluid the actual surgeon has elected to overfill. The virtual surgeon then further manipulates the splines of each breast area along the lines of the subject's chest wall contours, re-embedding each scaled virtual breast implant.

The virtual surgeon can also manipulate and shape the splines around the breast area to model the overfilled implant without changing the size/volume of the virtual breast implant. The estimated effects of settling and gravity can also be modeled, if desired.

Manipulation of the forecasted model(s) produces a modified forecasted model. The modified forecasted model is to be considered the most accurate predictive model as the virtual surgeon constructed this image using actual operational data, in collaboration with the actual surgeon.

The virtual surgeon then calculates and records the volume and surface area changes.

Figure 9:
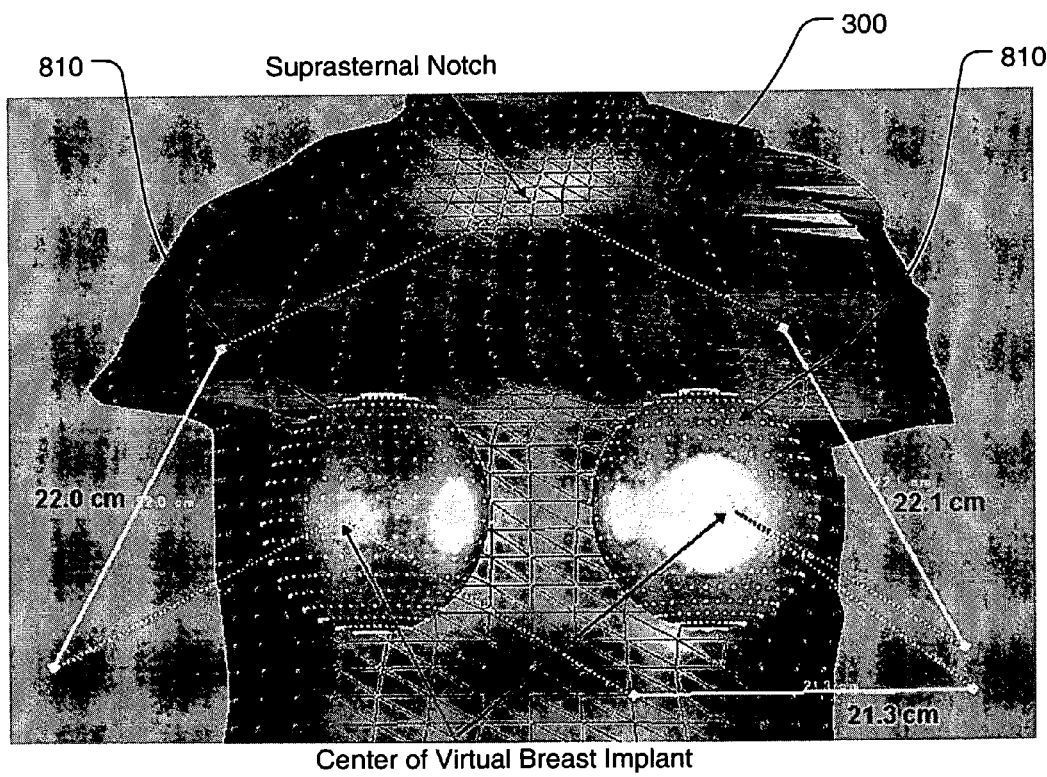
FIG. 9 shows the measurements that were used to locate the virtual breast implants on the subject's chest wall.

FIG. 9 shows exemplary virtual breast implants 810 located on the chest wall of the subject's preoperative VRML image 300. FIG. 9 also shows certain exemplary measurements used to locate the virtual breast implants 810 on the chest wall of the subject's preoperative VRML image 300.

As illustrated in FIG. 9, the virtual breast implants 810 are located on the chest wall of the subject's preoperative VRML image 300 using a measurement pattern.

As illustrated, the preoperative subject is approximately 153 cm in height, or around 5 feet. A general rule of thumb used by cosmetic surgeons for an aesthetic appearance of postoperative breast implants desires a measurement from the suprasternal notch to the center of the nipple complex of approximately 22 cm if the subject is 5 feet or less in height. If the subject is between 5 feet and 5 feet 6 inches, that measure should be approximately 23 cm. If the subject is between 5 feet 6 inches and 6 feet, that measure should be approximately 24 cm.

The nipple-to-nipple measurements should form a near equilateral triangle with the measurements made from the preoperative subject's suprasternal notch to the center of each virtual breast implant.

As illustrated in FIG. 9, the virtual breast implants 810 have been located on the chest wall of the subject's preoperative VRML image 300 according to the aesthetic rule of thumb for the optimal postoperative outcome, based on the height of the subject, with the measurement from the subject's suprasternal notch to the center of the nipple complex of approximately 22 cm and nipple-to-nipple measurement of 21 cm.

During placement of the virtual breast implants 810, the preoperative subject's actual nipple complex location and angle of protrusion must be noted and, if possible, duplicated. Most female subjects have a natural outward nipple protrusion of approximately 30 degrees, as measured from a center plane running through the subject's body from head to toe, the imaginary plane slicing the body in half, from top to bottom.

While most subjects generally have symmetric, 30 degree outwardly protruding nipple complexes, some preoperative subjects have more extreme outward nipple complex projections. The result of the actual surgical implant process generally does not correct this more extreme outward nipple complex projection. Rather, the actual breast implant process tends to proportionally maintain or magnify the more extreme outward nipple complex projections.

To model this condition, and to accurately position the virtual breast implants 810, the virtual surgeon utilizes the rotation functions of the native 3D data modeler.

Figure 10:
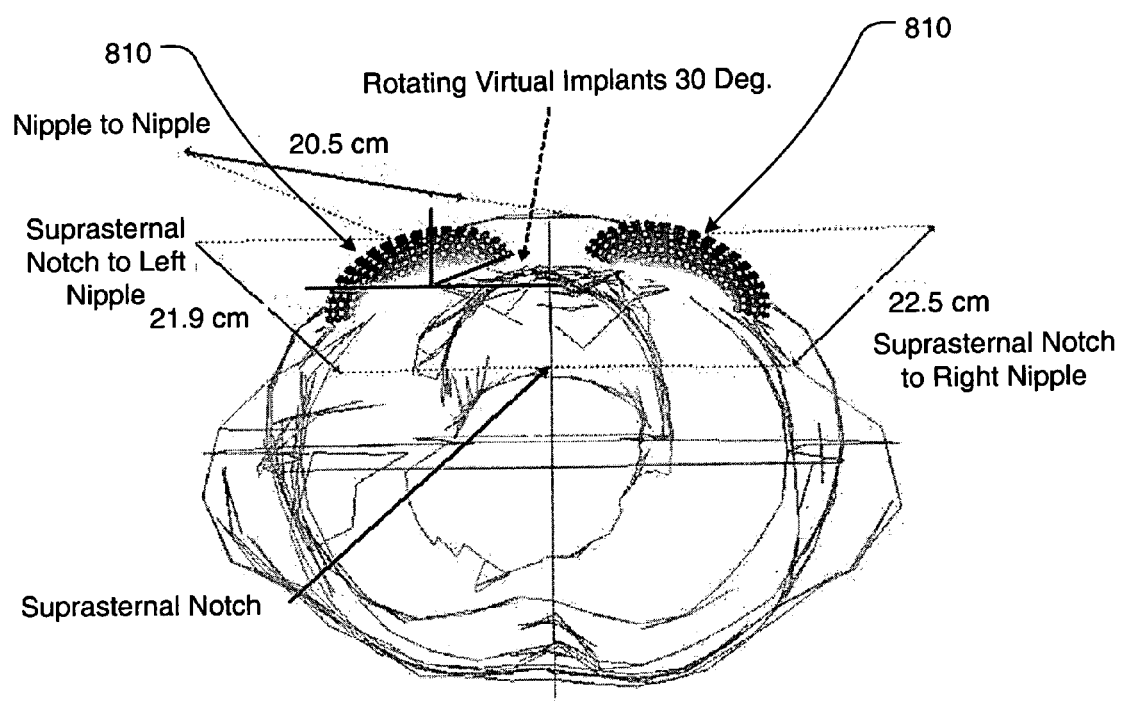
FIG. 10 shows the subject's torso in a supine position, with the virtual breast implants positioned in the correct location, based on the subject's preoperative typical 30 degree outward nipple protrusions.

As shown in FIG. 10, the preoperative subject's torso is modeled in a supine position, with the virtual breast implants 810 positioned in the correct location, based on the preoperative subject's preoperative typical 30 degree outward nipple protrusions. The torso is shown in a simplified view and the 30 degree measurement was made from a center plane running through the body, from the normal axis.

Figure 11:
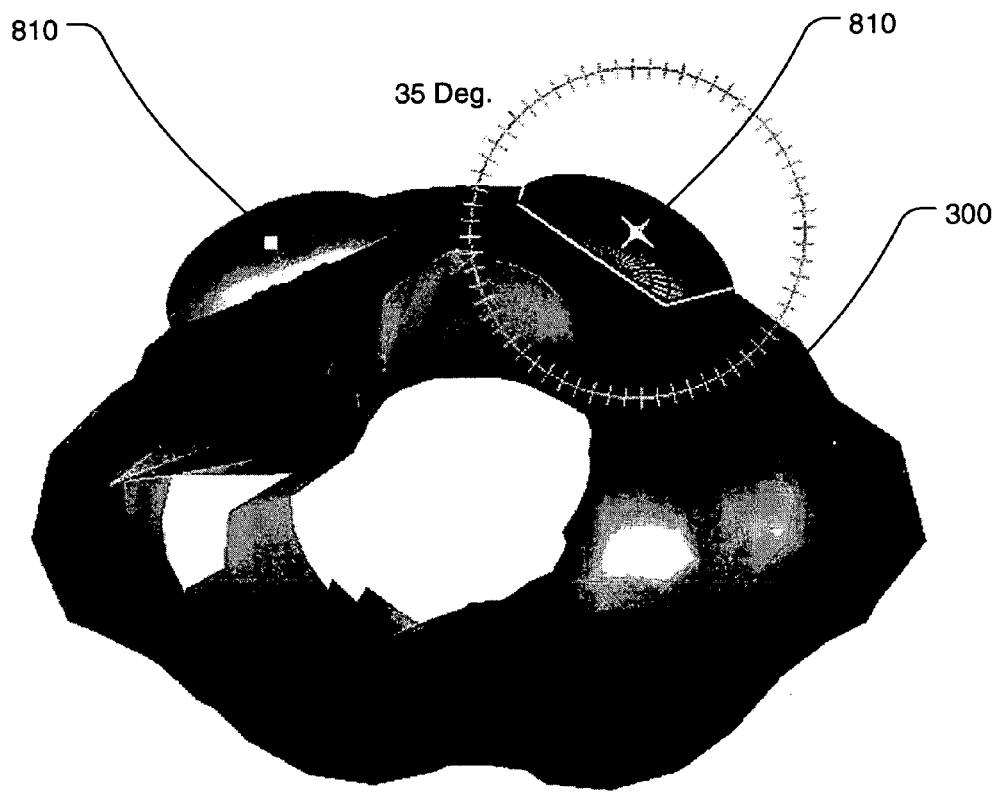
FIG. 11 shows the method of virtual breast implant rotation to accurately build a forecasted model of a subject that has more extreme outwardly projecting nipples.

FIG. 11 shows the method of virtual breast implant rotation to accurately build a forecasted model of a preoperative subject that has more extreme outwardly projecting nipple or nipple complex. As shown in FIG. 11, the right virtual breast implant has been rotated an additional 5 degrees to reflect a hypothetical preoperative subject's angle of nipple projection.

Once the virtual breast implants 810 are properly located on the chest wall of the subject's preoperative VRML image 300, the embedding process commences.

The embedding process consists of stretching and shaping the preoperative subject torso's points, edges, and facets until they seamlessly enclose the virtual breast implants 810. This can be done manually or automatically using the software program(s) incorporated in various exemplary embodiments of this invention.

Figure 12A:
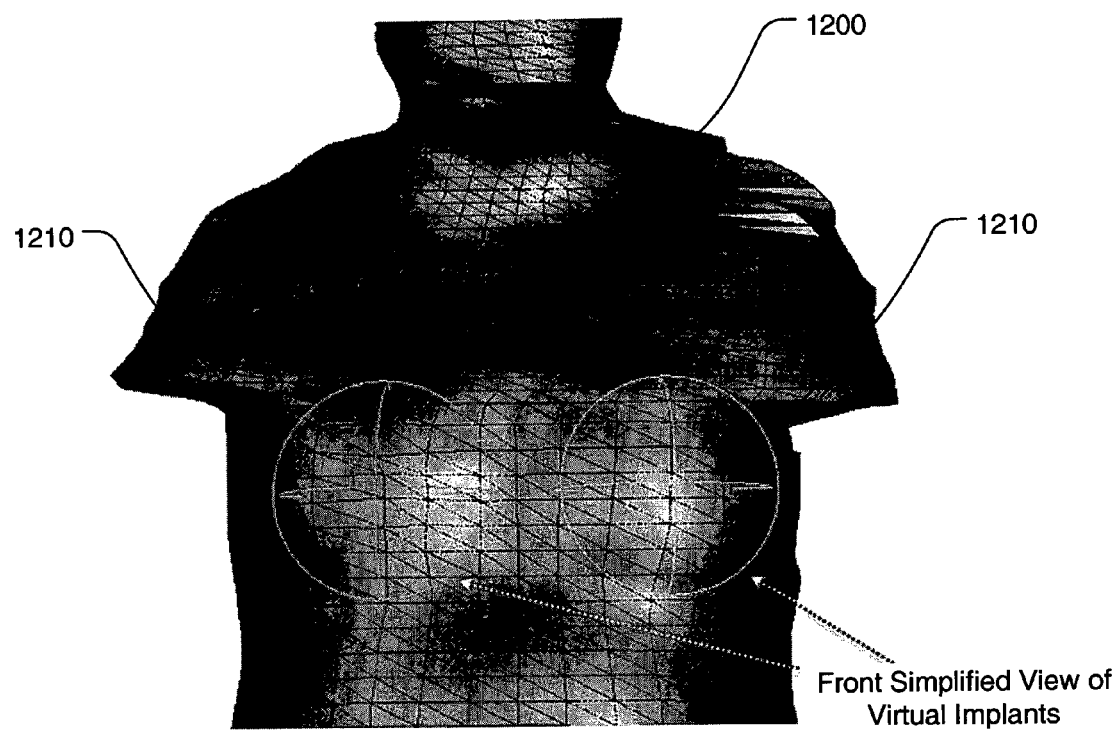
FIGS. 12A and 12B show the simplified view of virtual breast implants placed on the subject's chest wall.
Figure 12B:
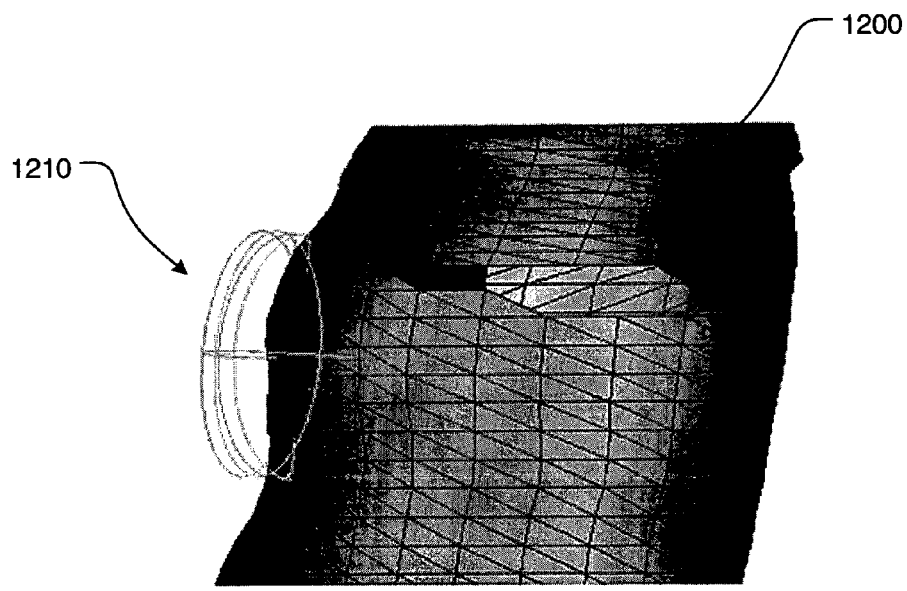
Figure 12C:
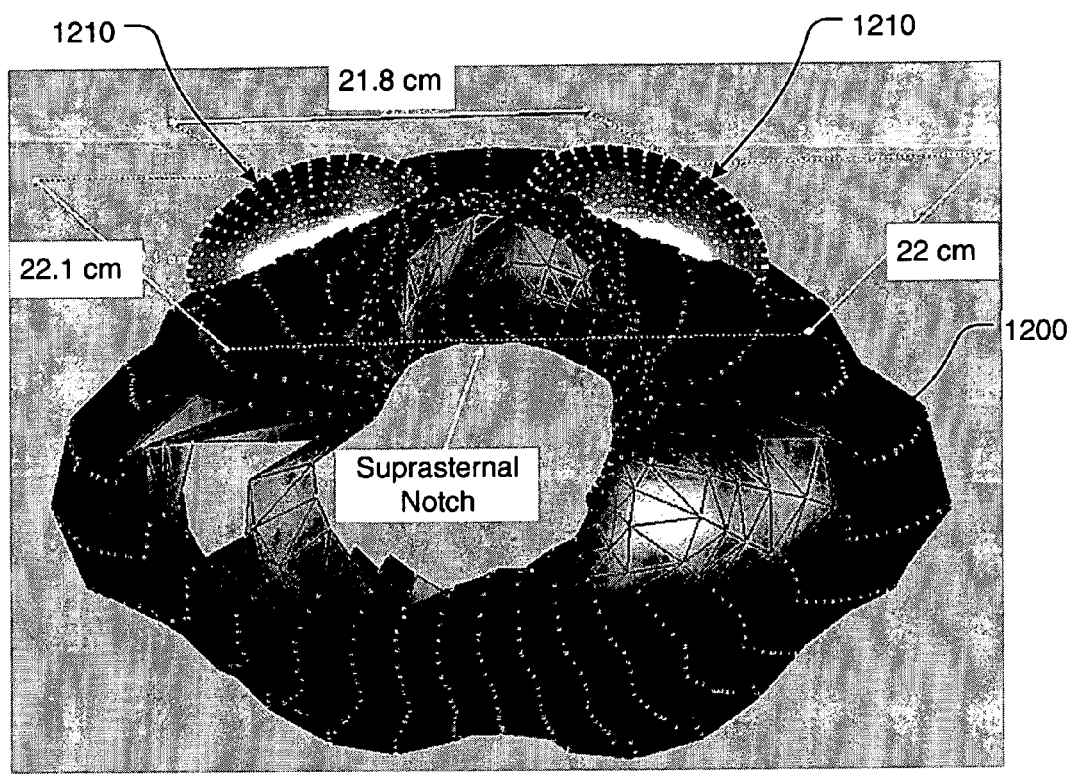
FIG. 12C shows a supine view of the simplified virtual breast implants.

FIGS. 12A, 12B, and 12C more clearly illustrate the embedding process by displaying the virtual breast implants 810 on the chest wall of the subject's preoperative VRML image 300 in a simplified view as opposed to a solid view.

The simplified view of the subject's preoperative VRML image 1200 contains the dimensional outlines of the virtual breast implants 1210.

FIGS. 12A, 12B, and 12C show a frontal simplified view, a side simplified view, and a supine simplified view, respectively, of the virtual breast implants 1210 placed on the chest wall of the subject's preoperative VRML image 1200.

The embedding process employs stretching and shaping tools to manipulate the points, edges, and facets of the subject's preoperative VRML image 1200 over the virtual breast implants 1210. Care is taken to align the splines along the contours of the virtual breast implants 1210. Misaligned splines show up clearly as a noticeable deformation of a surface contour.

It should be appreciated that the preoperative subject's initial torso volume and surface area are noted and recorded prior to manipulation.

In various exemplary embodiments, the embedding process is sequential, performed only on one virtual breast at a time. Alternatively, the embedding process may be performed on both virtual breasts at the same time. It should be understood that the embedding process can be done manually or under control of the software program(s) incorporated in various exemplary embodiments of this invention.

Figure 13:
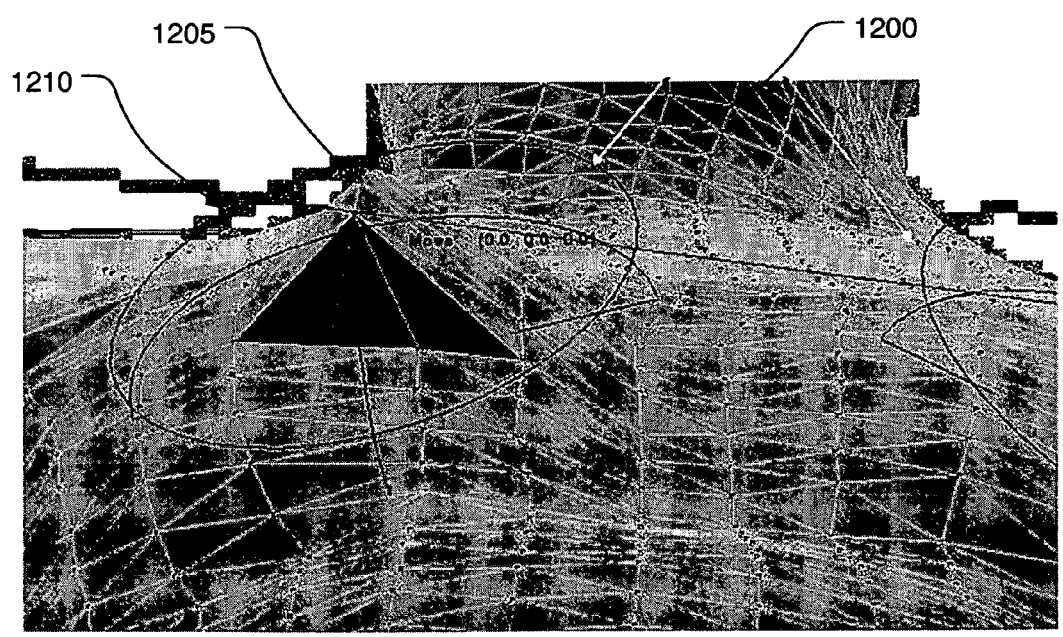
FIG. 13 shows the stretching and shaping process for embedding the right virtual breast implant.

FIG. 13 shows the stretching and shaping process for embedding the right virtual breast implant 1210 in the subject's preoperative VRML image 1200. Note that a spline 1205 of the subject's right breast has been elevated to a position that is slightly above the profile of the right virtual breast implant 1210.

Additional splines are manipulated and the embedding process continues until the outline of the virtual breast implant 1210 has been concealed within the subject's preoperative VRML image 1200. Embedding the virtual breast implant 1210 in this manner has the effect of maintaining the natural contours of the preoperative subject's torso, particularly along the lateral parts of the preoperative subject's chest wall.

Once a single virtual breast implant has been concealed, and the splines have been shaped to conform to the expanded space, the preoperative subject torso's volume and surface area are calculated and recorded.

These calculations closely predict the volumetric displacement of embedding an actual breast implant, along with the shape of the new actual breast and the contours of the actual breast area.

Figure 14:
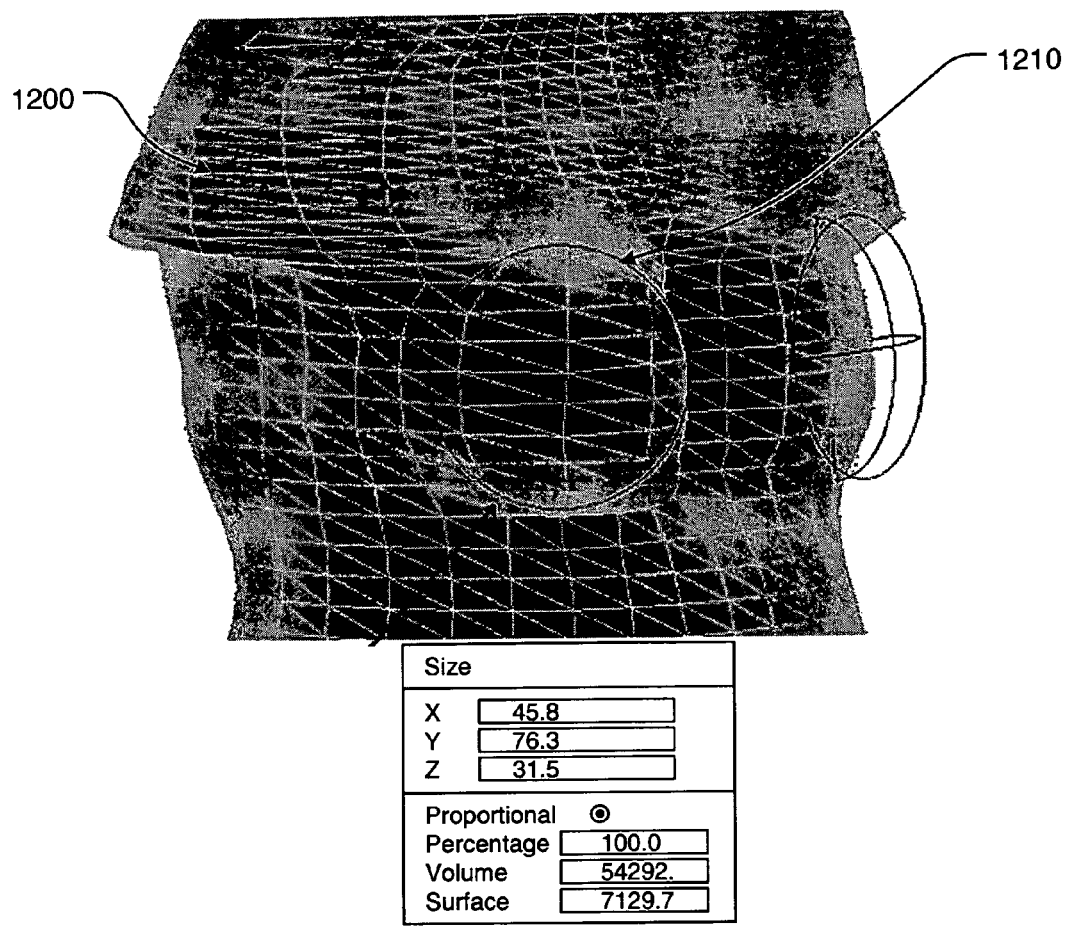
FIG. 14 shows the completion of embedding the virtual breast implant in the right breast, and the appropriate spline shaping, along with the updated volume and surface area calculations.

FIG. 14 shows the completion of the embedding process for the virtual breast implant 1210 in the right breast, and the appropriate spline shaping, along with the updated volume and surface area calculations.

The updated volume of the preoperative subject's torso is approximately 54,292 cubic centimeters, volume of the preoperative subject's torso prior to embedding the right virtual breast implant was approximately 53,967, reflecting a change of approximately 325 cubic centimeters, which is the approximate volume of the virtual breast implant.

Figure 15:
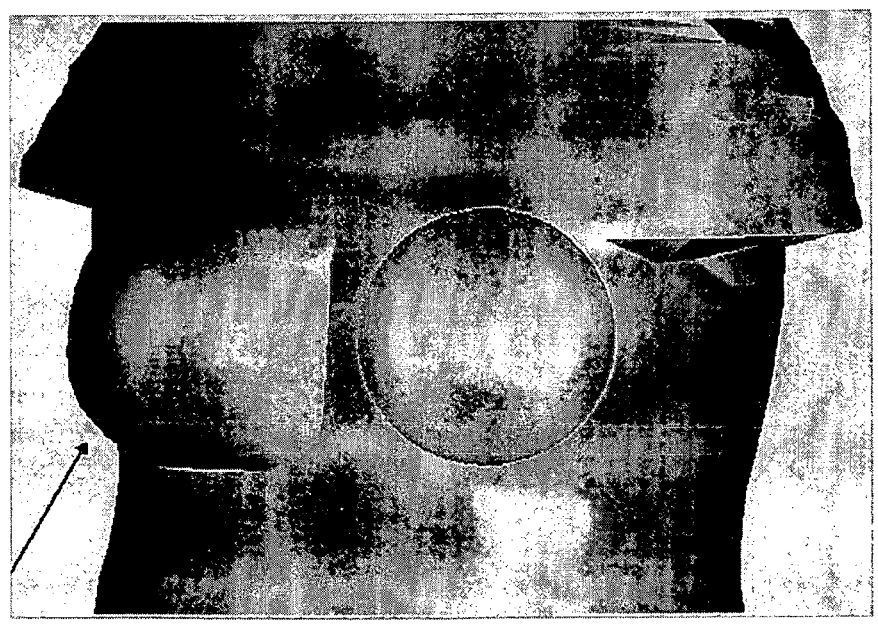
FIG. 15 shows the smoothed representation of the subject's updated torso.

FIG. 15 shows the smoothed representation of the updated torso of the subject's preoperative VRML image 1200.

The technique of embedding the virtual breast implant closely models the changes that the preoperative subject's breast undergoes as an actual breast implant is inserted during an actual surgical procedure.

In various exemplary embodiments of this invention, the virtual surgeon can model the effects of gravity and settling, if necessary or desired, by relocating the virtual breast implant's coordinates, expanding splines along a lower lateral portion of the implanted breast area, and contracting splines near an upper lateral portion of the implanted breast area. This can be accomplished with or without changing the total volume and surface area of the virtual breast implanted breast.

The decision to model gravity and settling effects depends largely on the age and condition of the preoperative subject. Younger preoperative subjects with good muscle tone and no preoperative ptotic symptoms generally maintain a consistent breast contour profile, once the associated swelling diminishes.

Older preoperative subjects with less muscle tone and less skin elasticity, or preoperative subjects with a ptotic preoperative breast condition are more susceptible to noticeable postoperative settling.

To model this condition, the virtual surgeon uses the initial nipple location measurement of the embedded virtual breast implant as a starting mark. The nipple complex is then relocated, moving the virtual breast implant lower down the torso.

Figure 16:
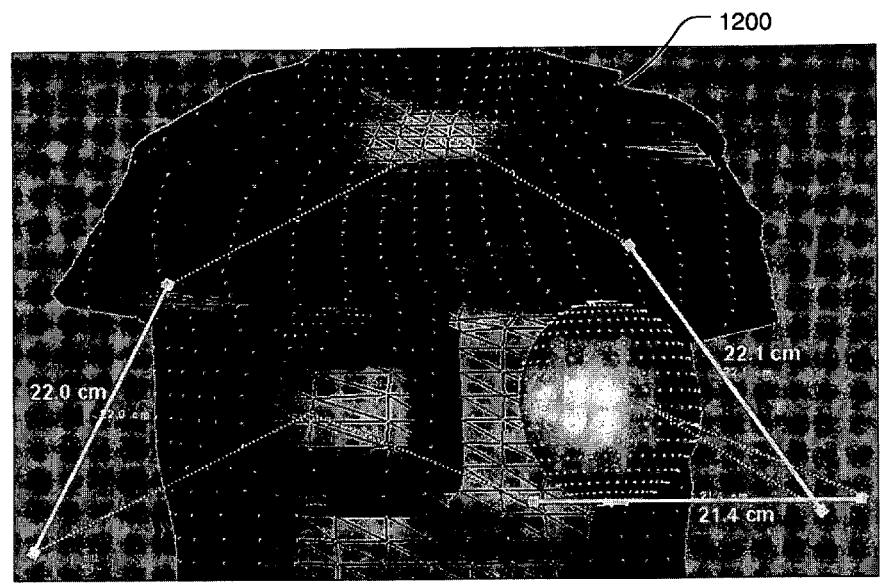
FIG. 16 shows the appropriate measurements used for embedding the right virtual breast implant.

As illustrated in FIGS. 16 through 19, a virtual breast implant can optionally be manipulated to model the effects of settling and gravity. FIG. 16 shows appropriate measurements used for embedding the right virtual breast implant 1210 in the subject's preoperative VRML image 1200. As shown in FIG. 16, the measurement point on the right breast reflects the predicted optimal nipple location.

Figure 17:
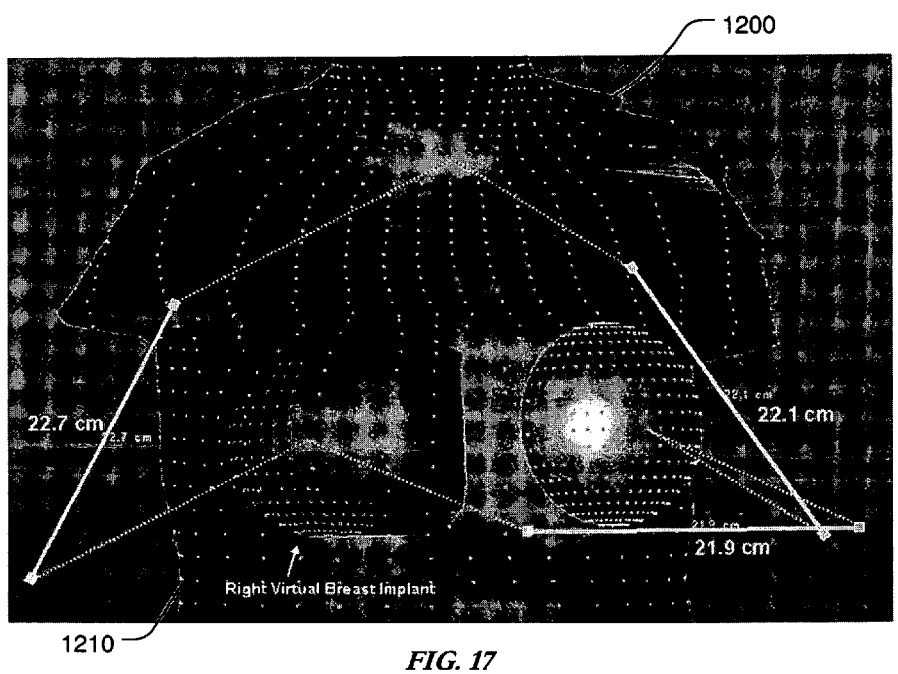
FIG. 17 shows the right virtual breast implant moved out along the x-axis and down along the z-axis to model the estimated effects of settling.

FIG. 17 shows the right virtual breast implant moved out along the x-axis an additional 0.5 cm and down along the z-axis 0.7 cm. This is a method to model the estimated effects of settling. The measurement from the preoperative subject's suprasternal notch to the nipple is now 22.7 cm, and the nipple-to-nipple measurement is 21.9 cm, reflecting an estimate of how the actual implants may settle within the preoperative subject.

Figure 18:
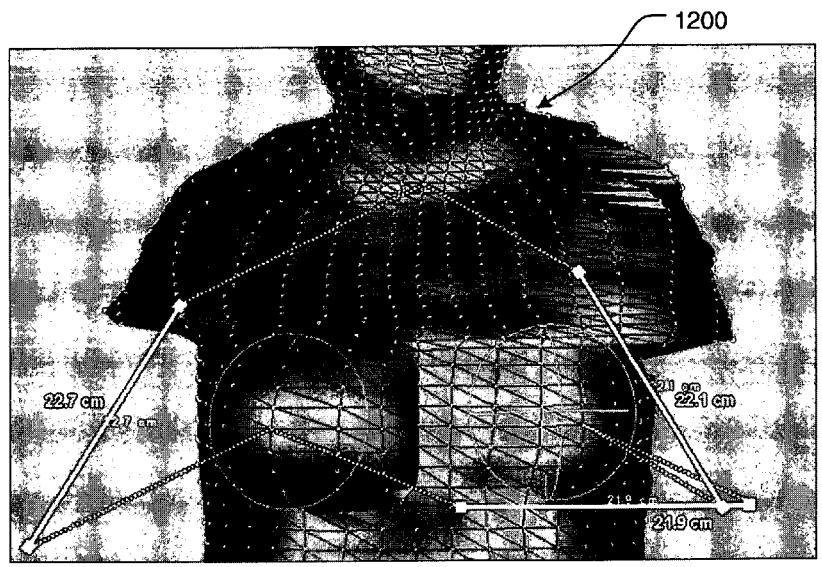
FIG. 18 shows the results of embedding the relocated right virtual breast implant, and associated measurements.

As illustrated in FIG. 18, the virtual surgeon manipulates the splines of the subject's preoperative VRML image 1200 to embed the relocated virtual breast implant 1210. Changes in contours around the upper breast area are also reflected.

FIG. 18 also shows certain of the associated measurements that result from embedding the relocated right virtual breast implant.

Figure 19:
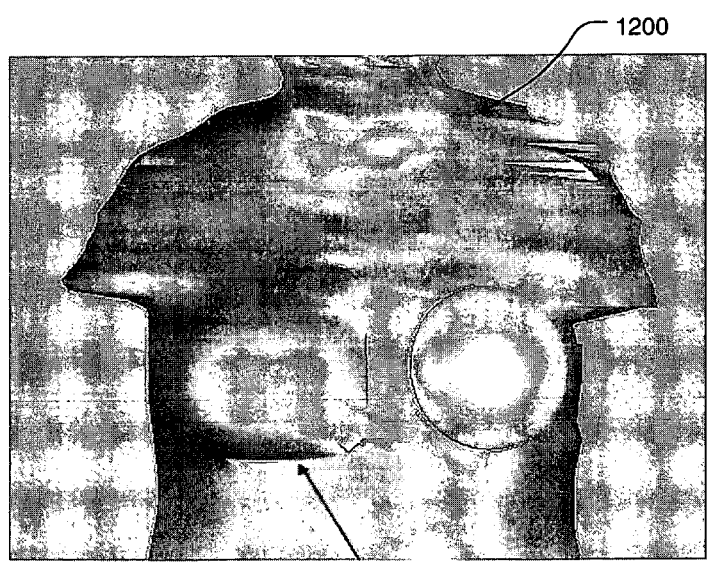
FIG. 19 shows a smoothed VRML view of the results of embedding the relocated right virtual breast implant of FIG. 18.

FIG. 19 shows a smoothed VRML view of the results of embedding the relocated right virtual breast implant of FIG. 18.

Once the first virtual breast, with the virtual breast implant embedded, has been modeled, the second breast then undergoes the virtual breast implant embedding process. The second virtual breast implant is embedded using the same stretching and shaping techniques, which can be performed manually or automatically by the software program(s) incorporated in various exemplary embodiments of this invention.

When the second virtual breast implant has been embedded, the torso volume and surface area of the subject's preoperative VRML image are then calculated and recorded.

Figure 20:
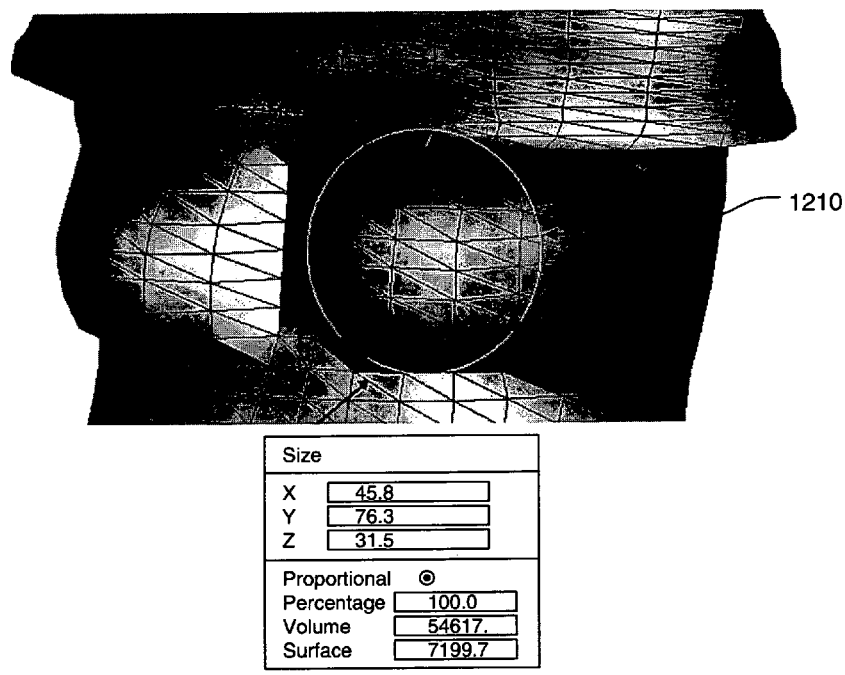
FIG. 20 shows the left virtual breast implant, in simplified view, and the subject's left breast of the torso stretched and shaped over the virtual breast implant, and the updated torso's volume and surface area calculations.

FIG. 20 shows the left virtual breast implant 1210, in simplified view, and the left virtual breast of the subject's preoperative VRML image 1200 stretched and shaped over the virtual breast implant 1210. The updated volume and surface area calculations for the subject's preoperative VRML image 1200 are also shown.

As illustrated in FIG. 20, the updated torso's volume and surface area has changed to reflect the volume addition of the left virtual breast implant. The difference in volume between the updated torso and the torso that had only the right virtual breast implant embedded is approximately 325 cubic centimeters, the surface area change between the two torsos is approximately 70.7 centimeters, squared.

It should again be appreciated that although the various exemplary embodiments described herein describe the virtual breast implant embedding process as being performed on one virtual breast at a time, the virtual breast implant embedding process can be performed on both virtual breasts simultaneously. Additionally, it should again be appreciated the virtual breast implants can optionally be manipulated to model the effects of settling and gravity.

Figure 21:
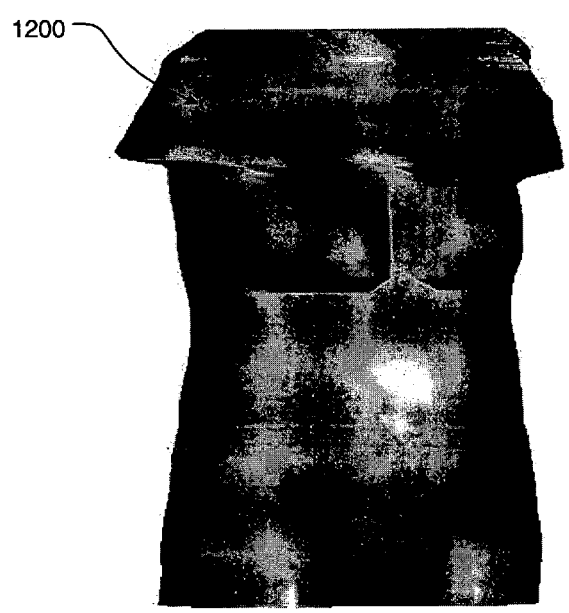
FIG. 21 shows the subject's completed torso in smoothed view after both virtual 325 cubic centimeters breast implants have been embedded.
Figure 22:
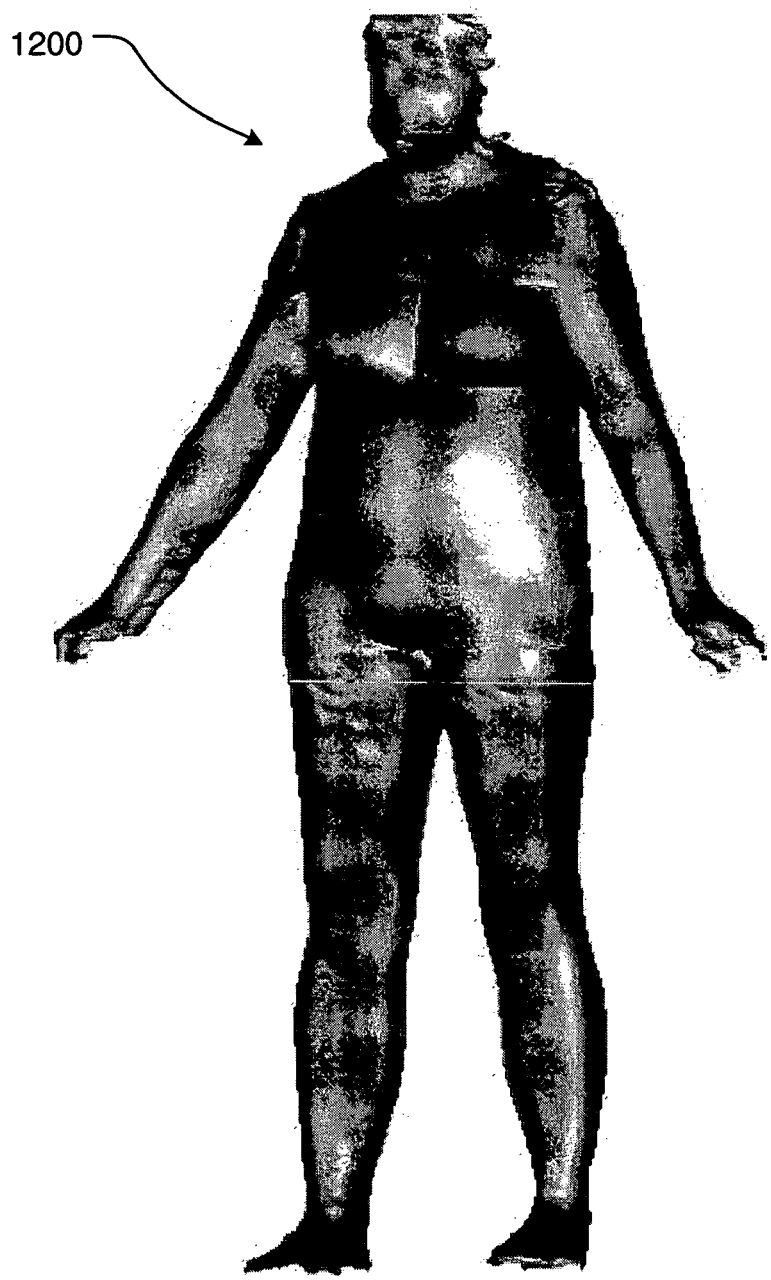
FIG. 22 shows the reassembled forecasted model, shown in smooth VRML view.

As shown in FIGS. 21 and 22, the subject's preoperative VRML image 1200, or a portion thereof, can then be displayed in a smooth mode to view any asymmetries, evaluate the aesthetic appeal, or adjust the amount of overfill fluid that the actual surgeon may desire to add.

While FIGS. 21 and 22 show "snapshots" of a 3-dimensional image. The systems and methods of this invention allow the virtual surgeon and/or the actual surgeon to view the subject's preoperative VRML image 1200, a 3-dimensional image, at multiple angles and various distances to closely inspect the results of embedding the volumetrically and dimensionally accurate virtual breast implants.

The subject's preoperative VRML image 1200 with the virtually embedded and manipulated virtual breast implants form the forecasted model. The forecasted model can be converted back to a format that the scanner software can interpret using, for example, a data converter software utility program.

Once the subject's preoperative VRML image is converted back to a scanner format, the forecasted model can be measured with the same MEP used to measure the preoperative scan image. Measurements are compared and evaluated. The forecasted model and the associated measurements are optionally placed into the preoperative subject's digital archive.

FIG. 23 shows the preoperative subject's VRML forecasted model converted into scanner software format. As further shown in FIG. 23, the same MEP used to measure the subject's preoperative scanned image 200 has been applied to the converted forecasted model 2300 and certain measurement lines 2310 have been applied to the converted forecasted model 2300 at, for example, the patient's chest, bust, underbust, waist, hips, abdomen, and stomach.

The chart 2320, as also shown in FIG. 23, shows an exemplary summary of certain of the measurements extracted by the procedure-specific MEP file. The measurements outlined in the chart 2320 include certain preoperative extracted measurements extrapolated from the converted forecasted model 2300.

The converted forecasted model can be reviewed by the actual surgeon and the preoperative subject prior to the actual surgery. The actual surgeon can use the converted forecasted model as a guideline during the actual surgical procedure.

In certain situations, after the forecasted model or the converted forecasted model has been reviewed, knowing the desires of the preoperative subject, and evaluating the symmetries of the actual preoperative subject, the actual surgeon elects to overfill one or both of the actual breast implants. For example, the actual surgeon may elect to overfill the left breast implant by 55 cubic centimeters and the right breast implant by 25 cubic centimeters.

If this occurs, either prior to or during an actual surgery, the systems and methods of this invention can model the overfilled breast implant. To accomplish this, the virtual surgeon selects one breast on the subject's preoperative VRML image and manipulates the splines to increase the volume and surface area of the virtual breast.

Figure 24:
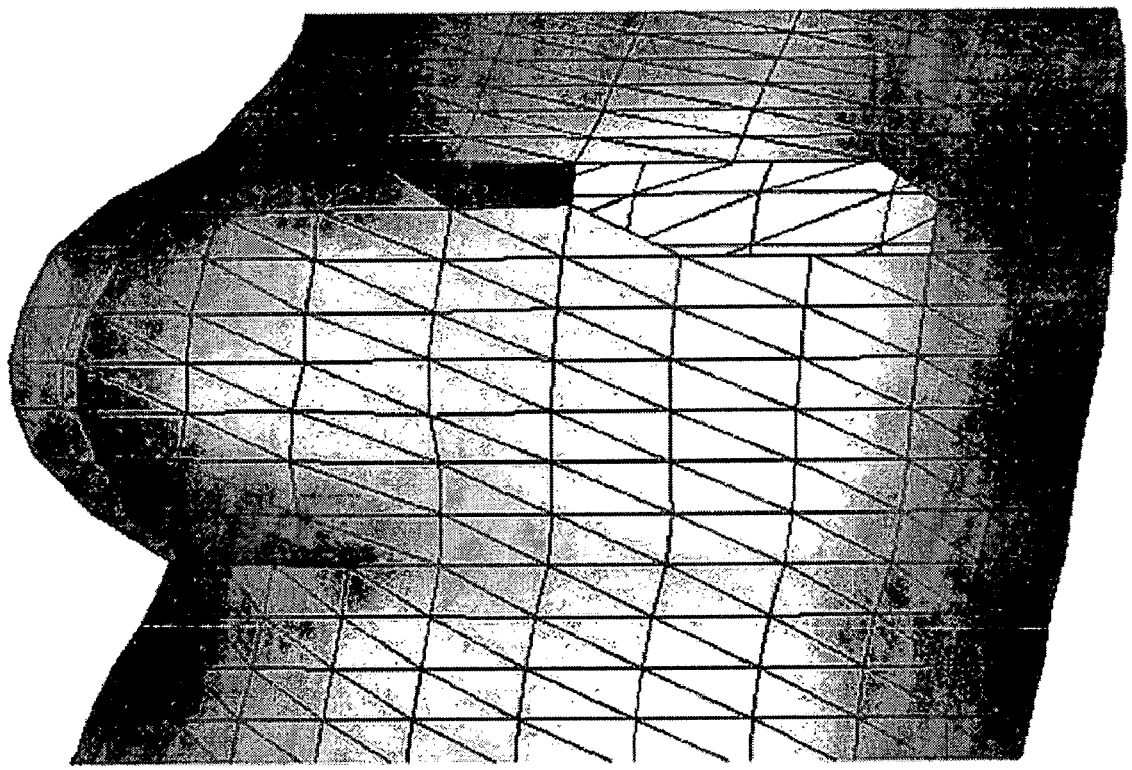
FIG. 24 shows the results of the right breast area of the subject's torso, after the splines have been manipulated, increasing the volume and surface area.

FIG. 24 shows the results of the right virtual breast area of the subject's preoperative VRML image, after the splines have been manipulated to increase the volume and surface area of the right virtual breast area. Note that the right virtual breast of the subject's preoperative VRML image has become larger than the preoperative subject's left virtual breast.

The volume and surface area calculations are also shown in FIG. 24. as illustrated, the change in volume as a result of manipulating the splines of the subject's preoperative VRML image displays an increase of 55 cubic centimeters.

The virtual surgeon then manipulates the splines of the left breast of the subject's preoperative VRML image to increase the volume by 25 cubic centimeters, modeling the amount of overfill fluid that the actual surgeon wishes to add to the initial 325 cubic centimeter implant.

Figure 25:
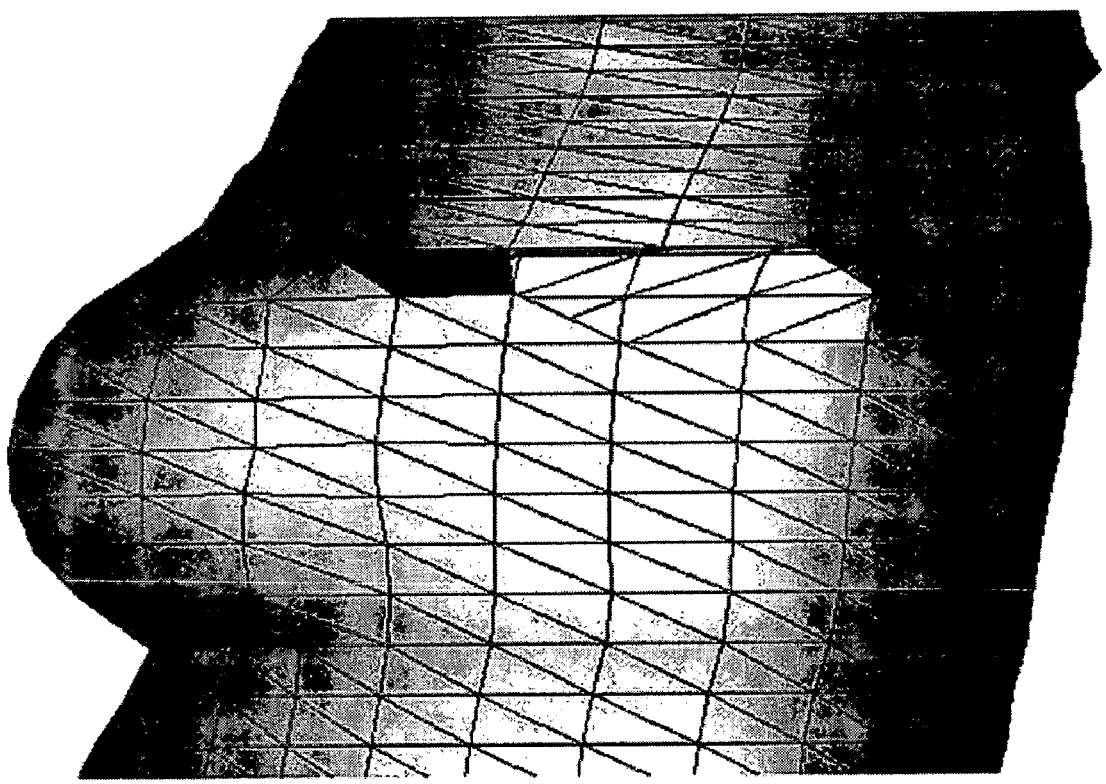
FIG. 25 shows the results of manipulating the splines of the left breast area of the subject's torso, increasing the volume of the torso's left breast by 25 cubic centimeters.

FIG. 25 shows the results of manipulating the splines of the left breast area of the subject's preoperative VRML image, increasing the volume of the left virtual breast by 25 cubic centimeters.

Note that the total volume change from the initial explanted torso is approximately 54,697-53,967, or 730 cubic centimeters, reflecting the right overfilled implant of approximately 380 cubic centimeters and the left overfilled implant of approximately 350 cubic centimeters.

The torso, if initially separated from the preoperative subject's VRML image is then reassembled with the remaining body parts that comprise the preoperative subject's VRML image.

Figure 26:
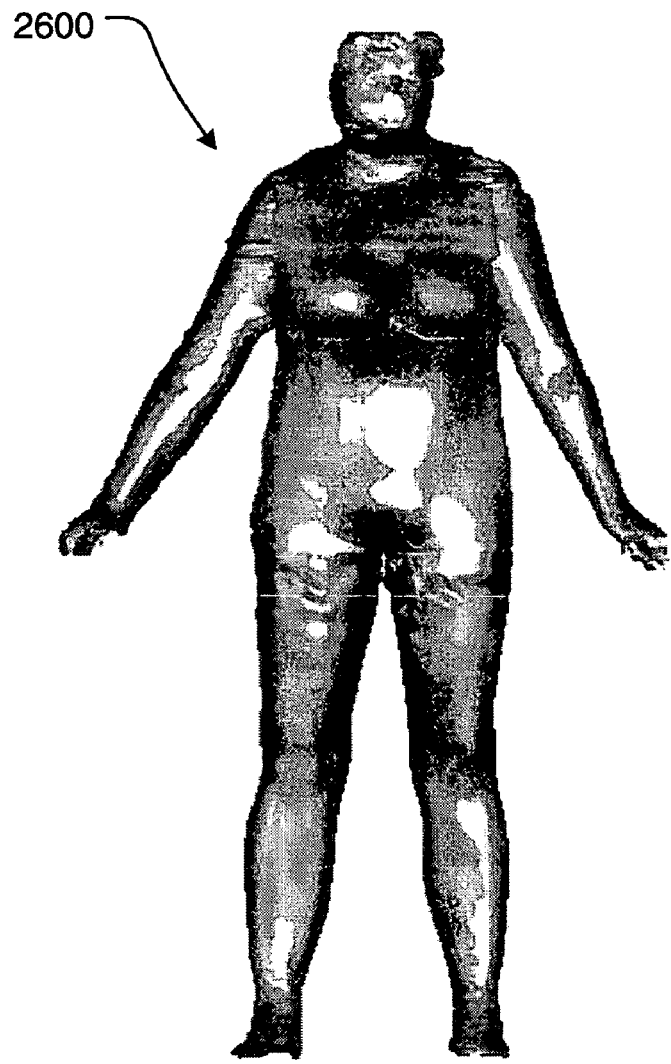
FIG. 26 shows the reassembled image, known as the modified forecasted model, as the virtual surgeon and the actual surgeon collaborated during the actual surgical procedure.

FIG. 26 shows the reassembled image, known as the modified forecasted model 2600. The actual surgeon can then view the modified forecasted model 2600 for aesthetic appeal prior to beginning or completing the actual surgical procedure.

As shown in FIG. 27, the modified forecasted model 2600 can then be converted to a scanner format using, for example, a data converter software utility. Once in scanner format, the modified forecasted image is measured using the same measurement extraction profile used to measure the preoperative scan image and the forecasted model, results are placed in the preoperative subject's digital archive.

FIG. 27 shows the modified forecasted model converted into scanner software format. As further shown in FIG. 27, the same MEP used to measure the subject's preoperative scanned image 200 has been applied to the modified converted forecasted model 2700 and certain measurement lines 2710 have been applied to the modified converted forecasted model 2700 at, for example, the patient's chest, bust, underbust, waist, hips, abdomen, and stomach.

The chart 2720, as also shown in FIG. 27, shows an exemplary summary of certain of the measurements extracted by the procedure-specific MEP file. The measurements outlined in the chart 2720 include certain preoperative extracted measurements extrapolated from the modified converted forecasted model 2700.

The modified converted forecasted model 2700 can be reviewed by the actual surgeon and/or the preoperative subject prior to or during the actual surgery. The actual surgeon can use the modified converted forecasted model 2700 as a modified guideline during the actual surgical procedure.

After the actual surgical procedure, the preoperative subject is scanned postoperatively, often on a repetitive basis. FIG. 28 shows the preoperative subject's two-week postoperative scan image 2800 and associated measurements 2810.

As further shown in FIG. 28, the same MEP used to measure the subject's preoperative scanned image 200 has been applied to the postoperative scan image 2800 and certain measurement lines 2810 have been applied to the postoperative scan image 2800 at, for example, the patient's chest, bust, underbust, waist, hips, abdomen, and stomach.

The chart 2820, as also shown in FIG. 28, shows an exemplary summary of certain of the measurements extracted by the procedure-specific MEP file. The measurements outlined in the chart 2820 include certain preoperative extracted measurements extrapolated from the postoperative scan image 2800.

The postoperative scan image 2800 can be reviewed by the actual surgeon and/or the preoperative subject, after the actual surgical procedure, to evaluate the results of the actual surgery and/or the validity of the forecasted model(s).

In various exemplary embodiments, the preoperative scan image measurements, forecasted model measurements, modified forecasted model measurements, and periodic postoperative scan image measurements are tabulated and presented for examination, analysis, comment and validation.

Table I shows a summary and comparison of certain of the measurements calculated from the preoperative scan, the forecasted model (having 325 cubic centimeter virtual breast implants), the modified forecasted model (having a 380 cubic centimeter left virtual breast implant and a 350 cubic centimeter right virtual breast implant), and the two-week postoperative scan.

TABLE I

Comparison of Measurements between preoperative scan, forecasted, modified forecasted and post-op scan images

| Measurement (cm) | Pre-op scan | FM | Δ | MFM | Δ Pre-op | Post-op scan | Δ MFM | Δ Pre-op |
|---|---|---|---|---|---|---|---|---|
| Height | 153.11 | 151.49 | | 151.24 | | 155.28 | | |
| Bust—Full | 105.48 | 104.38 | −1.10 | 105.29 | −0.19 | 106.67 | 1.37 | 1.18 |
| Bust—Full (Cont.) | 107.98 | 106.63 | −1.35 | 107.92 | −0.06 | 109.69 | 1.77 | 1.71 |
| Bust—Height | 112.65 | 112.62 | −0.03 | 112.54 | −0.11 | 112.61 | 0.06 | −0.04 |
| Bust—Width | 32.61 | 32.00 | −0.62 | 32.64 | 0.03 | 33.02 | 0.38 | 0.41 |
| BustProminence (L) | 28.87 | 29.19 | 0.32 | 29.41 | 0.53 | 31.74 | 2.34 | 2.87 |
| BustProminence (R) | 28.84 | 28.18 | −0.66 | 29.02 | 0.18 | 29.06 | 0.04 | 0.22 |
| Underbust—Full | 93.08 | 92.32 | −0.76 | 92.11 | −0.97 | 90.66 | −1.45 | −2.42 |
| Underbust—Width | 32.32 | 31.93 | −0.39 | 31.90 | −0.42 | 31.95 | 0.05 | −0.37 |
| Underbust—Height | 107.15 | 106.62 | −0.53 | 106.04 | −1.11 | 106.61 | 0.56 | −0.54 |
| FrontNeck2Bust (L) | 21.42 | 21.86 | 0.44 | 21.90 | 0.48 | 22.39 | 0.49 | 0.97 |
| FrontNeck2Bust (R) | 21.61 | 21.80 | 0.19 | 21.64 | 0.03 | 21.45 | −0.19 | −0.16 |
| SideNeck2Bust (L) | 28.12 | 30.76 | 2.64 | 27.34 | −0.78 | 28.09 | 0.75 | −0.03 |
| SideNeck2Bust (R) | 28.50 | 32.73 | 4.22 | 27.57 | −0.93 | 27.28 | −0.30 | −1.23 |
| Neck2BustLine (F) | 19.38 | 19.91 | 0.53 | 20.03 | 0.65 | 19.63 | −0.40 | 0.25 |
| Neck2BustLine (B) | 25.90 | 26.27 | 0.37 | 25.50 | −0.41 | 25.46 | −0.03 | −0.44 |
| BustToWaist (L) | 19.63 | 18.06 | −1.57 | 18.75 | −0.89 | 21.10 | 2.36 | 1.47 |
| BustToWaist (R) | 19.59 | 18.00 | −1.59 | 18.70 | −0.89 | 21.00 | 2.30 | 1.42 |
| BustToBust (H) | 19.01 | 18.51 | −0.50 | 17.60 | −1.41 | 20.79 | 3.19 | 1.78 |
| Chest—Full | 101.20 | 100.59 | −0.61 | 100.53 | −0.67 | 99.72 | −0.81 | −1.47 |
| Chest—Height | 118.65 | 118.37 | −0.28 | 119.54 | 0.89 | 119.11 | −0.44 | 0.46 |
| Chest—Width | 32.96 | 32.54 | −0.42 | 34.42 | 1.46 | 32.88 | −1.54 | −0.08 |
| Waist—Full | 99.00 | 97.76 | −1.25 | 97.72 | −1.29 | 95.49 | −2.23 | −3.51 |

Information similar to the summary information shown in Table I can be examined and analyzed, the actual surgeon and/or the virtual surgeon may add comments to the information if desired, and the information can be placed in the subject's digital archive.

Periodic postoperative scans may be made, measured, and appended to the subject's digital archive. Changes in the measurements will yield information about the preoperative subject's recovery as swelling abates and the breast implants settle.

Table II shows the volume and surface area of the changes of the preoperative subject, forecasted model, modified forecasted model, and postoperative scan.

TABLE II

Volume and Surface Area Comparisons

| Volume and Surface Area Analysis | Pre-op Torso | FM Torso | MFM Torso | Δ Pre-op | Post-op Torso | Δ MFM | Δ Pre-op Torso |
|---|---|---|---|---|---|---|---|
| Volume (cc) | 54,444 | 54,617 | 54,697 | 253 | 54,702 | 5 | 258 |

The postoperative scanned images are then added to a breast augmentation postoperative catalog database for future use per the methods described herein.

The interpretation of the surgical outcome is greatly enhanced by simultaneously viewing the preoperative subject's preoperative scan image, the forecasted model image(s), the modified forecasted model image (if available), and the postoperative scan image simultaneously, at known angles.

The native 3D data model files, in this exemplary embodiment VRML images, of the preoperative subject's preoperative scan image, the forecasted model(s), the modified forecasted model (if available), and the postoperative scan image are merged into a single file, spaced and annotated appropriately.

Lighting effects are applied within the software program(s) incorporated in various exemplary embodiments of this invention to highlight ambience, lighting direction, and light intensity, with appropriate shadow casting.

The equivalent of an isometric camera is then applied to view the composite image. An isometric camera views the scene from a plane rather than a point, eliminating any perspective distortions. In an isometric view, object size is not related to distance from the camera, every edge appears the size it actually is, and parallel lines appear parallel instead of tapering as they would in a perspective view.

It is understood that the modified forecasted image and the postoperative scan image need not be present to use this method. The virtual surgeon can prepare a forecasted model or models, and prepare a composite image containing the preoperative scan image and the forecasted model(s). A series of images can be rendered and presented to the surgeon and/or preoperative subject for review and evaluation prior to the surgical procedure.

FIGS. 29-34 show a series of images exemplary images that may be rendered from the composite data file(s).

Figure 29:
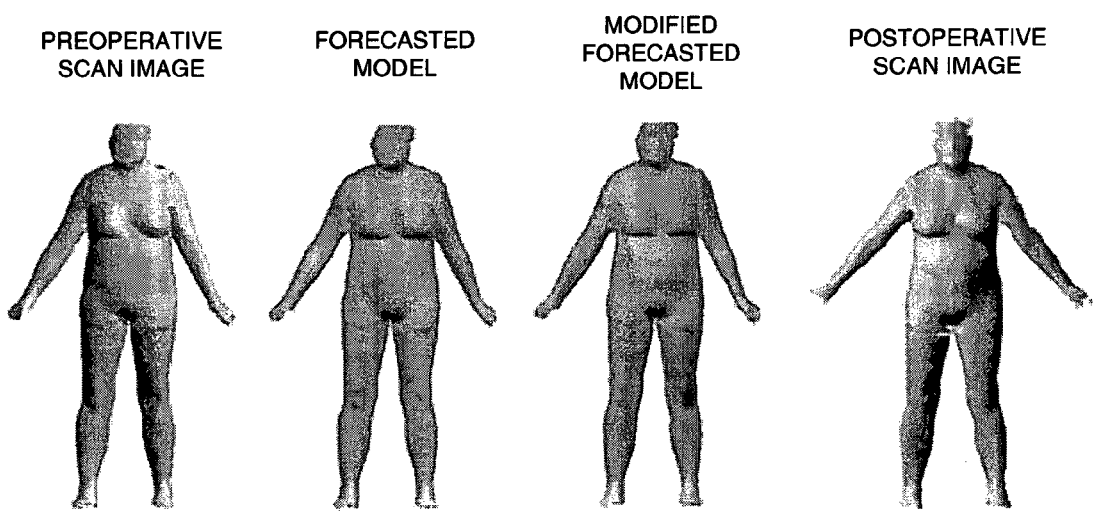
FIG. 29 shows a composite frontal view of preoperative, forecasted, modified forecasted and two-week postoperative images.

FIG. 29 shows a composite frontal view of preoperative, forecasted, modified forecasted and two-week postoperative images.

Figure 30:
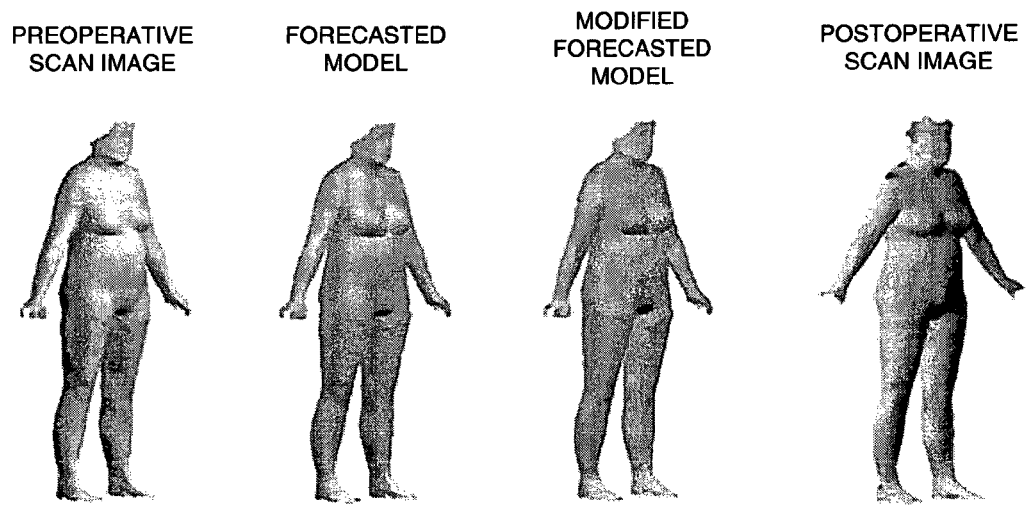
FIG. 30 shows the composite frontal view of preoperative, forecasted, modified forecasted and two-week postoperative images of FIG. 29, rotated 45 degrees.

FIG. 30 shows the composite frontal view of preoperative, forecasted, modified forecasted and two-week postoperative images of FIG. 29, rotated 45 degrees, wherein the right half-side profile of each image is highlighted.

Figure 31:
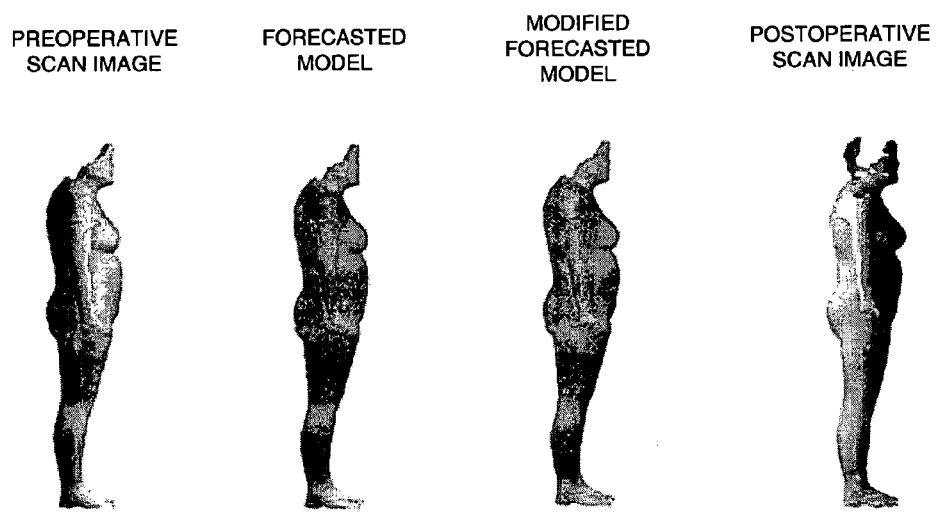
FIG. 31 shows the composite frontal view of preoperative, forecasted, modified forecasted and two-week postoperative images of FIG. 29, rotated 90 degrees.

FIG. 31 shows the composite frontal view of preoperative, forecasted, modified forecasted and two-week postoperative images of FIG. 29, rotated 90 degrees.

Figure 32:
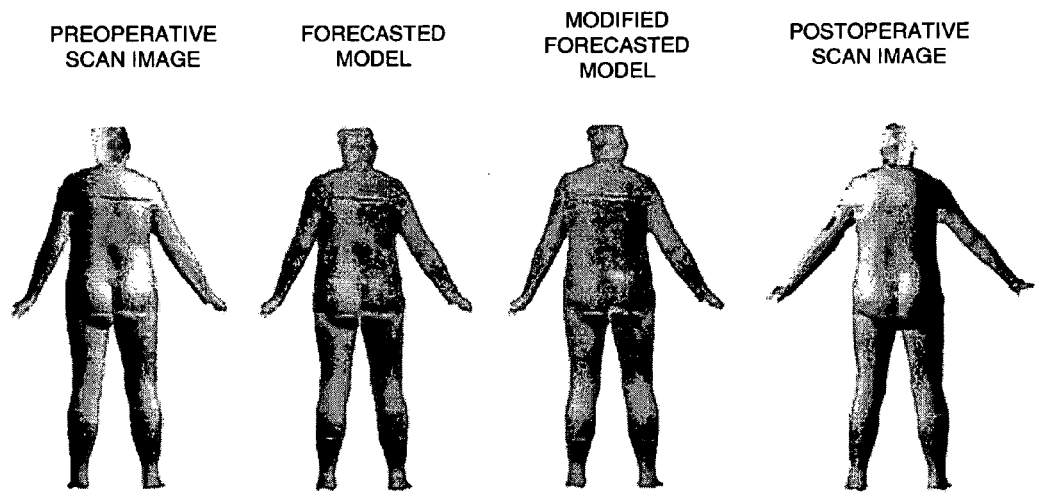
FIG. 32 shows the composite frontal view of preoperative, forecasted, modified forecasted and two-week postoperative images of FIG. 29, rotated 180 degrees.

FIG. 32 shows the composite frontal view of preoperative, forecasted, modified forecasted and two-week postoperative images of FIG. 29, rotated 180 degrees, wherein the back side of each image is highlighted.

Figure 33:
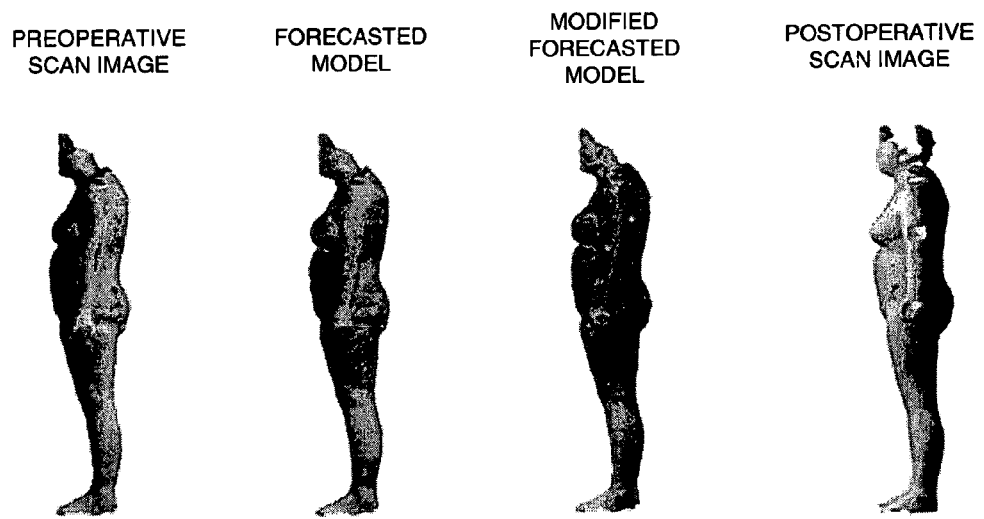
FIG. 33 shows the composite frontal view of preoperative, forecasted, modified forecasted and two-week postoperative images of FIG. 29, rotated 270 degrees.

FIG. 33 shows the composite frontal view of preoperative, forecasted, modified forecasted and two-week postoperative images of FIG. 29, rotated 270 degrees, wherein the right side of each image is highlighted.

Figure 34:
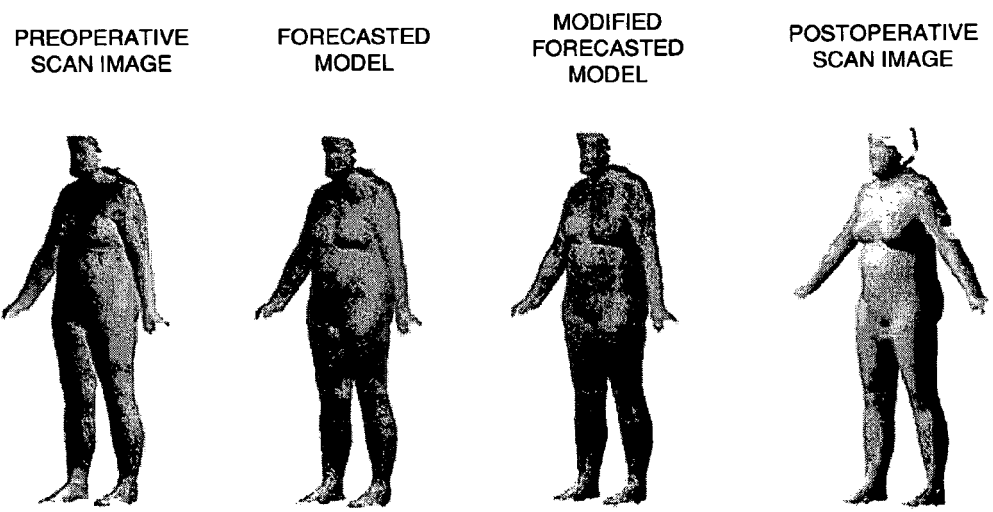
FIG. 34 shows the composite frontal view of preoperative, forecasted, modified forecasted and two-week postoperative images of FIG. 29, rotated 315 degrees.

FIG. 34 shows the composite frontal view of preoperative, forecasted, modified forecasted and two-week postoperative images of FIG. 29, rotated 315 degrees, wherein the left half-side of each image is highlighted.

While this invention has been described in conjunction with the exemplary embodiments outlined above, it is evident that many alternatives, modifications, and variations will be apparent to those skilled in the art.

For example, the embodiments of this invention have been described with reference to the prediction, evaluation, and validation of an exemplary breast augmentation surgical procedure. However, it should be appreciated that the virtual surgery systems, methods, and apparatuses of this invention may be utilized in various other cosmetic and reconstructive surgical procedures.

Such adaptations and modifications should and are intended to be comprehended within the meaning and range of equivalents of the disclosed exemplary embodiments.

It is to be understood that the phraseology of terminology employed herein is for the purpose of description and not of limitation. Accordingly, the foregoing description of the exemplary embodiments of the invention, as set forth above, are intended to be illustrative, not limiting. Various changes, modifications, and/or adaptations may be made without departing from the spirit and scope of this invention.

What is claimed is:

1. A method for performing virtual breast augmentation, comprising:

receiving a preoperative subject's scanned image, wherein the scanned image comprises a three dimensional image of at least the subject's complete torso;

converting the scanned image from a scanned image format to a three dimensional image modeling language format;

importing the converted three dimensional image into a three dimensional image editor;

receiving, from a breast implant database, at least one selected, modeled virtual breast implant, wherein the received virtual breast implant is selected based on a desired actual breast implant that is to be implanted in the preoperative subject, and wherein the virtual breast implant is a volumetrically and dimensionally accurate representation of an actual breast implant;

positioning the received virtual breast implant on a chest wall of the converted three dimensional image;

rotating the received virtual breast implant on the chest wall of the converted three dimensional image to accommodate an angle of a preoperative subject's nipple projection;

manipulating at least some of the splines of the converted three dimensional image to embed the virtual breast implant in the converted three dimensional image to create a manipulated three dimensional image; and displaying the manipulated three dimensional image.

2. The method of claim 1, wherein the breast implant database comprises a library of modeled virtual breast implants, which include the surface area and volume measurements for each of the virtual breast implants, such that the virtual breast implants can be used and manipulated by a three dimensional image editor.

3. The method of claim 1, wherein positioning the received virtual breast implant on a chest wall of the converted three dimensional image comprises adding at least some surface area or volume to the preoperative converted three dimensional image.

4. The method of claim 1, wherein manipulating at least some of the splines of the converted three dimensional image comprises utilizing stretching or shaping functions to manipulate at least some of the breast area points, edges, and facets of the converted three dimensional image over the received virtual breast implant.

5. The method of claim 1, further comprising manipulating at least some of the splines of the converted three dimensional image to model implant fluid overfill of the virtual breast implant in the converted three dimensional image.

6. The method of claim 1, further comprising displaying the received virtual breast implant in a simplified view once the received virtual breast implant is positioned on a chest wall of the converted three dimensional image, wherein the simplified view transparently displays the outlines of the profile of the received virtual breast implant.

7. The method of claim 1, further comprising modeling the effects of gravity and/or settling by relocating the coordinates of a nipple complex of the converted three dimensional image and manipulating at least some of the splines of the converted three dimensional image.

8. The method of claim 1, further comprising modeling the effects of gravity and settling by relocating the virtual breast implant's coordinates, expanding splines along a lower lateral portion of the implanted breast area, and contracting splines near an upper lateral portion of the implanted breast area.

9. The method of claim 1, further comprising converting the converted three dimensional image from a three dimensional image to a scanner-readable format to create a forecasted, scanner-readable image.

10. The method of claim 1, further comprising applying a Measurement Extraction Profile to the forecasted, scanner-readable image to determine at least some specific measurements of the forecasted, scanner-readable image.

11. The method of claim 1, wherein a first virtual breast implant is virtually embedded in the converted three dimensional image before a second virtual breast implant is virtually embedded in the converted three dimensional image.

12. The method of claim 1, wherein two virtual breast implants are virtually embedded in the converted three dimensional image simultaneously.

13. The method of claim 1, further including receiving at least some volumetric measurements to validate the converted three dimensional image.

14. The method of claim 1, further including receiving at least some surface area measurements to validate the converted three dimensional image.

* * * * *